United States Patent
Tassoni et al.

(10) Patent No.: US 12,186,493 B2
(45) Date of Patent: Jan. 7, 2025

(54) FLEXIBLE AND STRETCH RESISTANT ELONGATE SHAFT

(71) Applicant: BOSTON SCIENTIFIC SCIMED, INC., Maple Grove, MN (US)

(72) Inventors: Nicholas Lee Tassoni, Andover, MN (US); Ramon Libarnes, Plymouth, MN (US); Cory Ross Stenberg, St. Michael, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 18/422,583

(22) Filed: Jan. 25, 2024

(65) Prior Publication Data
US 2024/0157087 A1    May 16, 2024

Related U.S. Application Data

(62) Division of application No. 17/575,345, filed on Jan. 13, 2022, now Pat. No. 11,918,752.
(Continued)

(51) Int. Cl.
*A61M 25/00* (2006.01)
*B23P 11/02* (2006.01)
(Continued)

(52) U.S. Cl.
CPC .... *A61M 25/0009* (2013.01); *A61M 25/0012* (2013.01); *A61M 25/0014* (2013.01);
(Continued)

(58) Field of Classification Search
CPC . B23P 11/005; B23P 11/025; Y10T 29/49865; Y10T 29/49927; Y10T 29/4998;
(Continued)

(56) References Cited

U.S. PATENT DOCUMENTS

| 3,585,707 A | 6/1971 | Stevens |
| 4,791,963 A | 12/1988 | Gronert et al. |

(Continued)

FOREIGN PATENT DOCUMENTS

| EP | 2786711 A1 | 10/2014 |
| JP | 2007512914 A | 5/2007 |

(Continued)

OTHER PUBLICATIONS

International Search Report and Written Opinion dated May 17, 2022 for International Application No. PCT/US2022/012344.
(Continued)

*Primary Examiner* — Jermie E Cozart
(74) *Attorney, Agent, or Firm* — Seager, Tufte & Wickhem LLP

(57) ABSTRACT

A method of manufacturing an elongate shaft for delivery of a medical device may include disposing a polymeric sheath having a lumen extending therethrough over a mandrel; sliding a proximal portion of the polymeric sheath into a lumen of a metallic tubular member; placing a polymeric tubular member over the distal portion of the polymeric sheath and a distal portion of the metallic tubular member; fixedly attaching a proximal coupler to a distal end of a longitudinal support filament; inserting a proximal end of the longitudinal support filament between the polymeric sheath and the polymeric tubular member to position the longitudinal support filament alongside the distal portion of the metallic tubular member and a distal portion of the polymeric sheath; and reflowing the polymeric tubular member to secure the longitudinal support filament relative to the polymeric sheath and the metallic tubular member.

8 Claims, 21 Drawing Sheets

Related U.S. Application Data

(60) Provisional application No. 63/137,293, filed on Jan. 14, 2021.

(51) Int. Cl.
 *A61M 25/09* (2006.01)
 *B23P 11/00* (2006.01)

(52) U.S. Cl.
 CPC ........ *A61M 25/0043* (2013.01); *B23P 11/025* (2013.01); *A61M 25/0013* (2013.01); *A61M 2025/0063* (2013.01); *A61M 25/09025* (2013.01); *A61M 2205/02* (2013.01); *A61M 2207/10* (2013.01); *B23P 11/005* (2013.01); *Y10T 29/49865* (2015.01); *Y10T 29/49927* (2015.01); *Y10T 29/4998* (2015.01)

(58) Field of Classification Search
 CPC .......... A61M 25/0012; A61M 25/0014; A61M 25/0009; A61M 2207/10
 See application file for complete search history.

(56) References Cited

U.S. PATENT DOCUMENTS

| | | | |
|---|---|---|---|
| 5,470,315 A | 11/1995 | Adams | |
| 5,980,484 A | 11/1999 | Ressemann et al. | |
| 6,368,302 B1 | 4/2002 | Fitzmaurice et al. | |
| 7,815,625 B2 | 10/2010 | Stivland et al. | |
| 8,333,796 B2 | 12/2012 | Tompkins et al. | |
| 10,245,413 B2 | 4/2019 | Shimada et al. | |
| 2003/0125751 A1 | 7/2003 | Griffin et al. | |
| 2005/0115624 A1 | 6/2005 | Walak | |
| 2005/0182388 A1 | 8/2005 | Garabedian et al. | |
| 2005/0261666 A1 | 11/2005 | Larson | |
| 2014/0277084 A1 | 9/2014 | Mirigian et al. | |
| 2017/0151417 A1 | 6/2017 | Takemura et al. | |
| 2018/0296222 A1 | 10/2018 | Hebert et al. | |
| 2020/0205845 A1 | 7/2020 | Yang et al. | |

FOREIGN PATENT DOCUMENTS

| | | |
|---|---|---|
| JP | 2007520281 A | 7/2007 |
| JP | 2010533564 A | 10/2010 |
| JP | 2015502797 A | 1/2015 |
| JP | 2016511065 A | 4/2016 |
| WO | 1999065557 A2 | 12/1999 |
| WO | 2005072391 A2 | 8/2005 |
| WO | 2007121405 A2 | 10/2007 |
| WO | 200912362 A1 | 1/2009 |
| WO | 2015032292 A1 | 3/2015 |
| WO | 2020214221 A1 | 10/2020 |

OTHER PUBLICATIONS

"Embolize with confidence", AZUR Embolization System Brocure, 10 Pages, 2018.
Concerto Detachable Coils, Family Brochure, Medtronic, 4 Pages, 2018.

FLEXIBLE AND STRETCH RESISTANT ELONGATE SHAFT

CROSS REFERENCE TO RELATED APPLICATIONS

The present application is a divisional of U.S. patent application Ser. No. 17/575,345, filed Jan. 13, 2022, which claims the benefit of and priority to U.S. Prov. Patent App. No. 63/137,293, filed Jan. 14, 2021, each titled FLEXIBLE AND STRETCH RESISTANT ELONGATE SHAFT, the disclosures of which are incorporated herein by reference.

TECHNICAL FIELD

The present disclosure pertains to medical devices and methods for manufacturing and/or using medical devices. More particularly, the present disclosure pertains to configurations of a flexible and stretch resistant elongate shaft and methods of making a flexible and stretch resistant elongate shaft.

BACKGROUND

A wide variety of intracorporeal medical devices have been developed for medical use, for example, surgical and/or intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. There is an ongoing need to provide alternative medical devices as well as alternative methods for manufacturing and/or using medical devices.

SUMMARY

In a first example, a method of manufacturing an elongate shaft for delivery of a medical device may comprise: disposing a polymeric sheath having a lumen extending therethrough over a mandrel; sliding a proximal portion of the polymeric sheath into a lumen of a metallic tubular member; placing a polymeric tubular member over the distal portion of the polymeric sheath and a distal portion of the metallic tubular member; fixedly attaching a proximal coupler to a distal end of a longitudinal support filament; inserting a proximal end of the longitudinal support filament between the polymeric sheath and the polymeric tubular member to position the longitudinal support filament alongside the distal portion of the metallic tubular member and a distal portion of the polymeric sheath; and reflowing the polymeric tubular member to secure the longitudinal support filament relative to the polymeric sheath and the metallic tubular member.

In addition or alternatively to any example disclosed herein, a distal portion of the longitudinal support filament is positioned against an outer surface of the distal portion of the polymeric sheath. In addition or alternatively to any example disclosed herein, proximal portion of the longitudinal support filament is positioned against an outer surface of the distal portion of the metallic tubular member. In addition or alternatively to any example disclosed herein, the method may comprise: before reflowing the polymeric tubular member, engaging the proximal coupler with a distal end of the polymeric sheath. In addition or alternatively to any example disclosed herein, the medical device includes a distal coupler configured to axially overlap and releasably engage the proximal coupler.

In addition or alternatively to any example disclosed herein, the method may comprise: after reflowing the polymeric tubular member, removing the mandrel from the lumen of the polymeric sheath; and thereafter disposing a release wire axially within the lumen of the polymeric sheath, and through the proximal coupler and the distal coupler to releasably couple the medical device to the proximal coupler. In addition or alternatively to any example disclosed herein, the polymeric tubular member includes a proximal portion formed from a first polymeric material and a distal portion formed from a second polymeric material different from the first polymeric material. In addition or alternatively to any example disclosed herein, the method may comprise: after reflowing the polymeric tubular member, applying a hydrophobic coating to an outer surface of the polymeric tubular member. In addition or alternatively to any example disclosed herein, the longitudinal support filament is a metallic wire.

In addition or alternatively to any example disclosed herein, the metallic tubular member includes a proximal portion and a distally tapered portion extending from the proximal portion to the distal portion. In addition or alternatively to any example disclosed herein, after reflowing the polymeric tubular member, a proximal-most end of the polymeric tubular member is disposed distal of the distally tapered portion of the metallic tubular member. In addition or alternatively to any example disclosed herein, the method may comprise: before reflowing the polymeric tubular member, positioning a tubular heat shrink member over the polymeric tubular member. In addition or alternatively to any example disclosed herein, an outer surface of the polymeric sheath is etched.

In addition or alternatively to any example disclosed herein, and in a second example, a method of manufacturing an elongate shaft for delivery of a medical device may comprise: extruding a polymeric tubular member and a longitudinal support filament over a first polymeric sheath disposed on a mandrel to form a composite tubular member; sliding a metallic tubular member over a second polymeric sheath and securing a distal end of the second polymeric sheath to a distal end of the metallic tubular member; placing the composite tubular member, with the mandrel removed, over a distal portion of the metallic tubular member; and reflowing a proximal portion of the polymeric tubular member onto the distal portion of the metallic tubular member to secure the longitudinal support filament relative to the metallic tubular member.

In addition or alternatively to any example disclosed herein, a proximal portion of the first polymeric sheath is removed from within the composite tubular member before placing the composite tubular member over the distal portion of the metallic tubular member. In addition or alternatively to any example disclosed herein, reflowing the proximal portion of the polymeric tubular member secures the longitudinal support filament against an outer surface of the distal portion of the metallic tubular member. In addition or alternatively to any example disclosed herein, the method may comprise: fixedly attaching a proximal coupler to a distal end of the longitudinal support filament. In addition or alternatively to any example disclosed herein, a distal portion of the polymeric tubular member is removed to expose the distal end of the longitudinal support filament prior to fixedly attaching the proximal coupler.

In addition or alternatively to any example disclosed herein, an elongate shaft for delivery of a medical device may comprise a polymeric sheath having a lumen extending therethrough; a metallic tubular member disposed over a proximal portion of the polymeric sheath; a polymeric tubular member disposed over a distal portion of the polymeric sheath and a distal portion of the metallic tubular member; a longitudinal support filament extending along the distal portion of the polymeric sheath and the distal portion of the metallic tubular member; and a proximal coupler fixedly attached to a distal end of the longitudinal support filament. The polymeric tubular member may secure the longitudinal support filament relative to the polymeric sheath and the metallic tubular member. The polymeric tubular member may include a proximal portion, a distal portion, and a middle portion having a lower bending stiffness than the proximal portion and the distal portion. The longitudinal support filament may extend within the proximal portion, the middle portion, and the distal portion of the polymeric tubular member. The longitudinal support filament may substantially prevent axial stretching of the polymeric tubular member.

In addition or alternatively to any example disclosed herein, the middle portion defines a preferential bending location of the elongate shaft.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
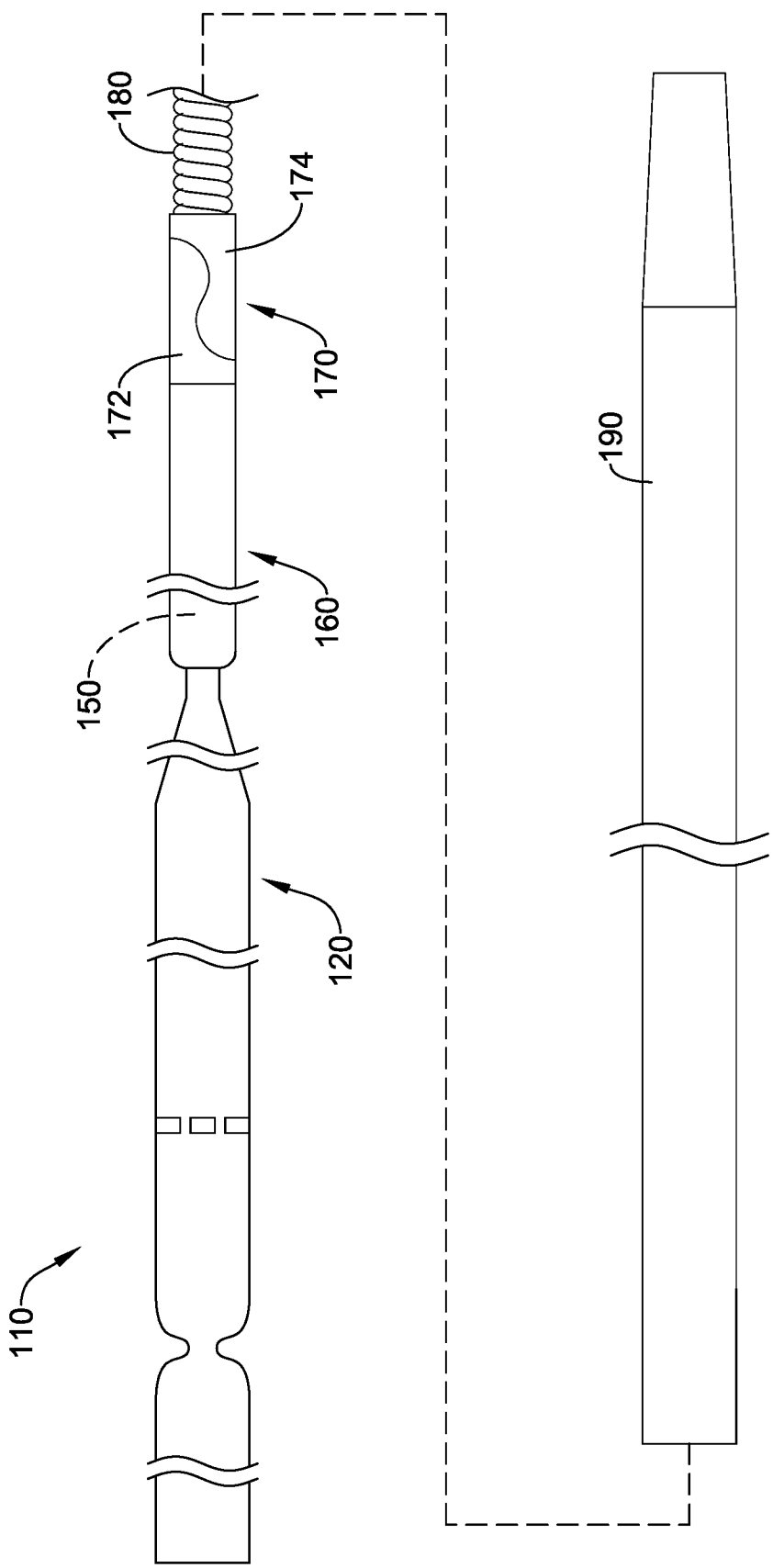
FIG. 1 illustrates aspects of a medical device system including a delivery shaft.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the present disclosure. Those skilled in the art will recognize that the various elements described and/or shown may be arranged in various combinations and configurations without departing from the scope of the disclosure. The detailed description and drawings illustrate example embodiments of the disclosure. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified. The recitation of numerical ranges by endpoints includes all numbers within that range, including the endpoints (e.g., 1 to 5 includes 1, 1.5, 2, 2.75, 3, 3.80, 4, and 5). Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the present disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art. For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

FIG. 1 illustrates aspects of a medical device system. The medical device system may include an elongate shaft 110 having a lumen extending from a proximal portion of the elongate shaft 110 to a distal end of the elongate shaft 110. In some embodiments, the elongate shaft 110 may be a tubular and/or annular structure defined by a wall having an inner surface and an outer surface. In some embodiments, the lumen may extend along and/or may be coaxial with a central longitudinal axis of the elongate shaft 110. In some embodiments, the elongate shaft 110 may have a substantially constant and/or uniform outer extent and/or outer diameter along at least a portion of its length. Other configurations, including but not limited to the elongate shaft 110 having one or more tapers, steps, and/or changes in outer extent and/or outer diameter, are also contemplated. In some embodiments, the elongate shaft 110 may have an overall length of about 120 centimeters (cm), about 150 cm, about 170 cm, about 180 cm, about 190 cm, about 200 cm, about 210 cm, about 230 cm, or another suitable overall length depending upon the intended procedure. Some suitable materials for the elongate shaft 110, for example metallic materials, polymer materials, composite materials, etc., are described below.

A medical device 180 may be disposed proximate, adjacent, and/or at the distal end of the elongate shaft 110. The medical device 180 may be releasably attached to the distal end of the elongate shaft 110. In some embodiments, the medical device 180 may be disposed distal of the distal end of the elongate shaft 110. For simplicity, the medical device 180 is illustrated herein as a shape memory embolic coil, such as those used to treat aneurysms for example, but other suitable medical devices transported, delivered, used, released, etc. in a similar manner are also contemplated, including but not limited to stents, embolic filters, replacement heart valves, occlusion devices, and/or other medical implants, etc. Some suitable but non-limiting materials for the medical device 180, for example metallic materials, polymeric materials, composite materials, etc., are described below.

In some embodiments, the medical device system may include a microcatheter 190 including a lumen therein sized and configured to deliver the medical device 180 to a treatment site. In at least some embodiments, a distal end of the elongate shaft 110 may be configured to be disposed within a proximal end of the lumen of the microcatheter 190 to facilitate advancement of the elongate shaft 110 and/or the medical device 180 within the lumen of the microcatheter 190. The elongate shaft 110 and the medical device 180 may be configured to be slidably disposed within the lumen of the microcatheter 190. In some embodiments, the elongate shaft 110 and the medical device 180 may be advanced through the lumen of the microcatheter 190 for deployment of the medical device 180 at the treatment site. In some embodiments, the microcatheter 190 may facilitate percutaneous delivery of the medical device 180 to the treatment site. In FIG. 1, the medical device 180 is shown in a delivery configuration, wherein the medical device 180 is substantially aligned with, coaxial with, and/or colinear with the elongate shaft 110 and/or the central longitudinal axis of the elongate shaft 110. In at least some embodiments, the medical device 180 may be positioned and/or arranged in a substantially elongated configuration in the delivery configuration. Other configurations are also contemplated.

In some embodiments, the medical device 180 may be configured to assume and/or shift to a deployed configuration when unconstrained (e.g., in situ, etc.). In some embodiments, the medical device 180 may be heat set in the deployed configuration using a shape memory material such that upon delivery to the treatment site, the patient's body heat and/or temperature causes the medical device 180 to shift to the deployed configuration when unconstrained (by the microcatheter 190, for example) and/or when released from the elongate shaft 110. Some suitable but non-limiting materials for the microcatheter 190, for example metallic materials, polymeric materials, composite materials, etc., are described below. In some embodiments, the medical device 180 may be shifted into the deployed configuration manually, such as by the use of selective electrical, chemical, and/or magnetic stimulation, a pull wire, etc. In some embodiments, the medical device 180 may be shifted into the deployed configuration automatically, such as by the use of shape memory materials or other suitable methods. The medical device 180 may be shifted into the deployed configuration at any suitable and/or desired time after the medical device 180 has been advanced beyond the distal end of the microcatheter 190.

In some embodiments, a release mechanism 170 may be configured to releasably attach the medical device 180 to the distal end of the elongate shaft 110. In some embodiments, the elongate shaft 110 may include a proximal coupler 172 of the release mechanism 170 fixedly attached to the distal end of the elongate shaft 110 and the medical device 180 may include a distal coupler 174 of the release mechanism 170 fixedly attached to a proximal end of the medical device 180. A distal end of a release wire 186 (e.g., FIG. 12) may slidably engage with the proximal coupler 172 of the release mechanism 170 and the distal coupler 174 of the release mechanism 170. The release wire 186 may interlock the proximal coupler 172 of the release mechanism 170 with the distal coupler 174 of the release mechanism 170 when the first portion 130 of the metallic tubular member 120 is engaged with the second portion 140 of the metallic tubular member 120 and/or when the release wire 186 is in the first position, as described herein. For example, when the first portion 130 of the metallic tubular member 120 is disengaged and/or separated from the second portion 140 of the metallic tubular member 120, the release wire 186 may be translated in a proximal direction relative to the elongate shaft 110 to release the distal coupler 174 of the release mechanism 170 and/or the medical device 180 from the proximal coupler 172 of the release mechanism 170 and/or the elongate shaft 110. In at least some embodiments, the release wire 186 may be slidably disposed within the elongate shaft 110, the proximal coupler 172 of the release mechanism 170, and the distal coupler 174 of the release mechanism 170. Some suitable but non-limiting materials for the release mechanism 170, the proximal coupler 172, and/or the distal coupler 174, for example metallic materials, polymer materials, composite materials, etc., are described below.

In some embodiments, the elongate shaft 110 may include several component parts that combine to form the elongate shaft 110. In some embodiments, the elongate shaft 110 may include a polymeric sheath 150, a metallic tubular member 120, and a polymeric tubular member 160. In some embodiments, the elongate shaft 110 may include additional and/or other component parts and/or elements, as discussed herein. Construction of the elongate shaft 110 is discussed herein and relative positioning and features of each element of the elongate shaft 110 will be apparent. Some of the features discussed herein are shown in FIG. 1 for reference but are discussed in more detail with respect to subsequent figures. Some suitable but non-limiting materials for the polymeric sheath 150, the metallic tubular member 120, and/or the polymeric tubular member 160 are described below.

Figure 2:
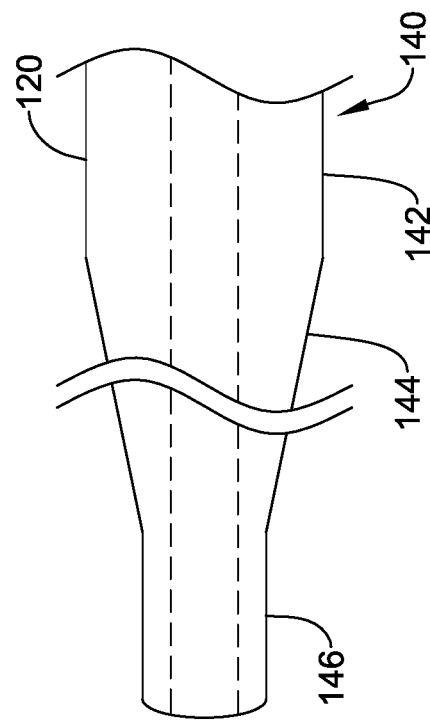
FIGS. 2-12 illustrate aspects of a reflow method of manufacturing a delivery shaft.
Figure 2:
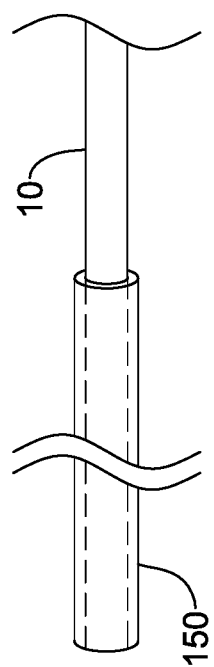

FIGS. 2-12 relate to a method of manufacturing the elongate shaft 110 for delivery of the medical device 180. As seen in FIG. 2, the method may include disposing the polymeric sheath 150 having a lumen extending therethrough on and/or over a mandrel 10. In some embodiments, the polymeric sheath 150 may be slidably disposed over the mandrel 10. In some embodiments, the polymeric sheath 150 may be formed directly on the mandrel 10. For example, the polymeric sheath 150 may be extruded onto the mandrel 10. In another example, the polymeric sheath 150 may be formed as a tubular structure and the mandrel 10 may be inserted into the polymeric sheath 150 (or the polymeric sheath 150 may be slid over the mandrel 10). In one example, the polymeric sheath 150 may have an outer diameter of about 0.006 inches (about 0.1524 millimeters). In other examples, the polymeric sheath 150 may have an outer diameter of about 0.004 inches (0.1016 millimeters) to about 0.008 inches (about 0.2032 millimeters). The mandrel 10 may be removable from the polymeric sheath 150, as discussed herein. In some embodiments, the mandrel 10 may be slidable with respect to the polymeric sheath 150. In some embodiments, the polymeric sheath 150 may have a slight friction fit and/or a slight interference fit with the mandrel 10 (e.g., the mandrel 10 may not move freely relative to the polymeric sheath 150) that may be overcome at a later time to remove the mandrel 10 from the lumen of the polymeric sheath 150. In one example, the polymeric sheath 150 may be formed from polytetrafluoroethylene (PTFE). Other materials are also contemplated. In at least some embodiments, an outer surface of the polymeric sheath 150 may be etched and/or otherwise mechanically or chemically treated to facilitate bonding and/or securement to another polymeric material.

The method may include sliding a proximal portion of the polymeric sheath 150 into a lumen of the metallic tubular member 120, wherein the proximal portion of the polymeric sheath 150 is disposed within the metallic tubular member 120 and a distal portion of the polymeric sheath 150 is disposed distal of the metallic tubular member 120. In some embodiments, the method may include sliding the proximal portion of the polymeric sheath 150 into a distal end of the lumen of the metallic tubular member 120 and advancing the proximal portion of the polymeric sheath 150 at least partially through the metallic tubular member 120. In one example, the lumen of the metallic tubular member 120 may have an inner diameter of about 0.008 inches (about 0.2032 millimeters). In other examples, the lumen of the metallic tubular member 120 may have an inner diameter of about 0.006 inches (about 0.1524 millimeters) to about 0.010 inches (about 0.254 millimeters). In at least some embodiments, the lumen of the metallic tubular member 120 may have a substantially constant inner diameter along its entire length.

The metallic tubular member 120 may include a first portion 130 and a second portion 140. The first portion 130 of the metallic tubular member 120 may be disposed proximal of a pre-defined break region 122 (e.g., FIGS. 1, 12) formed in the metallic tubular member 120. The second portion 140 of the metallic tubular member 120 may be disposed distal of the pre-defined break region 122 formed in the metallic tubular member 120. In at least some embodiments, the second portion 140 of the metallic tubular member 120 may include a proximal portion 142, a tapered portion 144, and a distal portion 146. The proximal portion 142 of the second portion 140 of the metallic tubular member 120 may have a first outer diameter, the distal portion 146 of the second portion 140 of the metallic tubular member 120 may have a second outer diameter that is less than the first outer diameter, and the tapered portion 144 may taper gradually and/or continuously in a distal direction from the proximal portion 142 and/or the first outer diameter to the distal portion 146 and/or the second outer diameter. In some embodiments, the tapered portion 144 may be referred to as a distally tapered portion, and thus the metallic tubular member 120 may include the proximal portion 142, the distal portion 146, and the distally tapered portion (ref. 144) extending from the proximal portion 142 to the distal portion 146. In one example, the metallic tubular member 120 may be formed from nickel-titanium alloy (e.g., nitinol). Other materials are also contemplated.

In some embodiments, the metallic tubular member 120 may have an overall length of about 97 centimeters (cm), about 127 cm, about 140 cm, about 155 cm, about 167 cm, about 175 cm, about 190 cm, about 207 cm, or another suitable overall length depending upon the intended procedure. In one example, the distal portion 146 of the second portion 140 of the metallic tubular member 120 may have a length of about 5 cm. In other examples, the distal portion 146 of the second portion 140 of the metallic tubular member 120 may have a length of about 3.5 cm to about 6.5 cm. In one example, the tapered portion 144 of the second portion 140 of the metallic tubular member 120 may have a length of about 15 cm. In other examples, the tapered portion 144 of the second portion 140 of the metallic tubular member 120 may have a length of about 12 cm to about 18 cm.

In one example, the first portion 130 of the metallic tubular member 120 may have an outer diameter of about 0.018 inches (about 0.4572 millimeters). In other examples, the first portion 130 of the metallic tubular member 120 may have an outer diameter of about 0.015 inches (about 0.381 millimeters) to about 0.021 inches (about 0.5334 millimeters). In one example, the proximal portion 142 of the second portion 140 of the metallic tubular member 120 may have an outer diameter of about 0.018 inches (about 0.4572 millimeters). In other examples, the proximal portion 142 of the second portion 140 of the metallic tubular member 120 may have an outer diameter of about 0.015 inches (about 0.381 millimeters) to about 0.021 inches (about 0.5334 millimeters). In one example, the distal portion 146 of the second portion 140 of the metallic tubular member 120 may have an outer diameter of about 0.0105 inches (about 0.2667 millimeters). In other examples, the distal portion 146 of the second portion 140 of the metallic tubular member 120 may have an outer diameter of about 0.008 inches (about 0.2032 millimeters) to about 0.012 inches (about 0.3048 millimeters).

Figure 3:
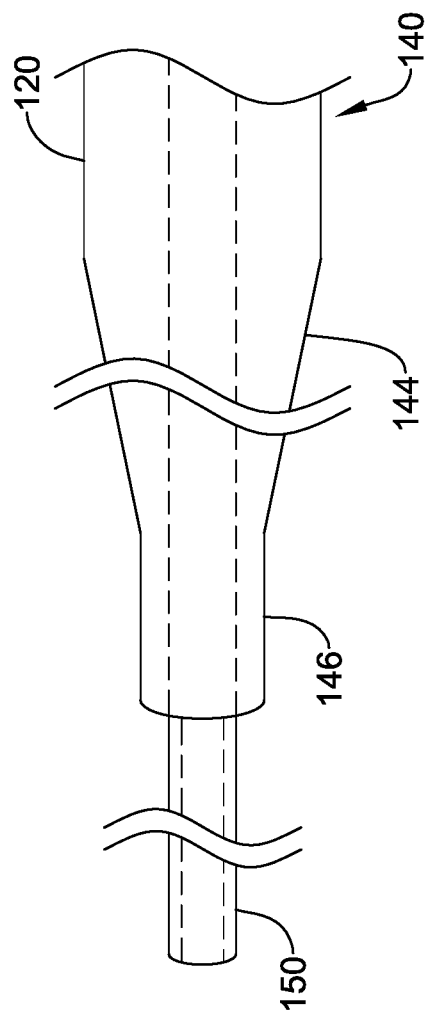
Figure 3:
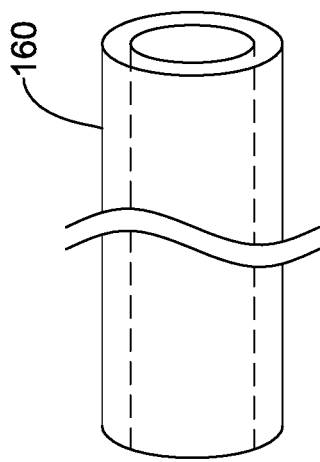
Figure 4:
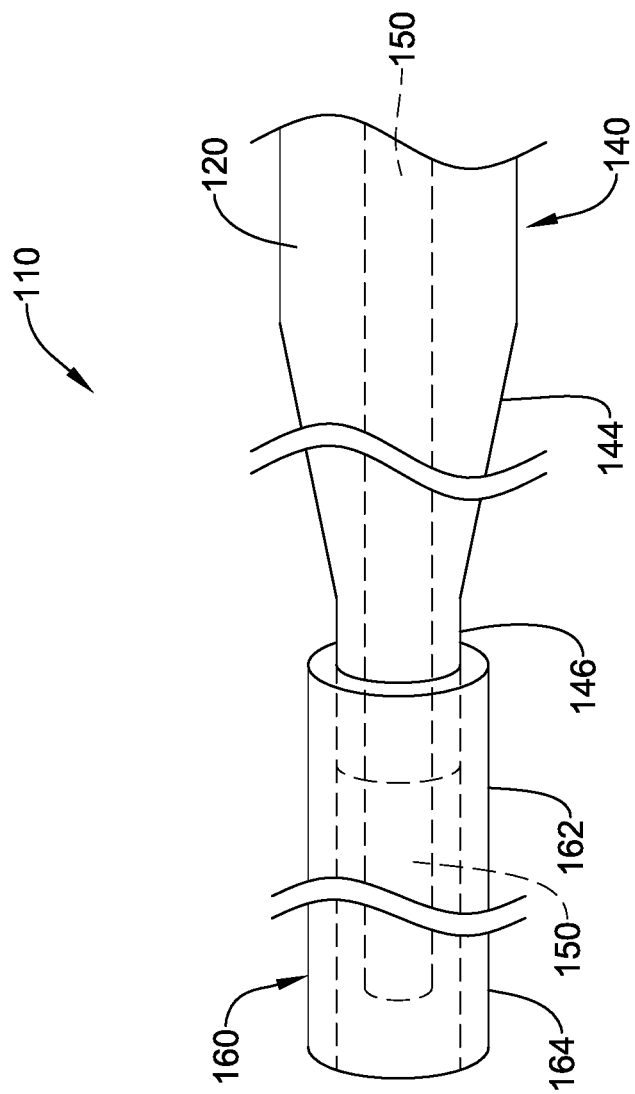

As seen in FIGS. 3 and 4, the method may include placing a polymeric tubular member 160 over the distal portion of the polymeric sheath 150 and the distal portion 146 of the second portion 140 of the metallic tubular member 120. In some embodiments, a flaring mandrel (not shown) may be inserted into a proximal end of the polymeric tubular member 160 to widen the proximal end of the polymeric tubular member 160 prior to placing the proximal end of the polymeric tubular member 160 over the distal portion 146 of the second portion 140 of the metallic tubular member 120. The proximal end of the polymeric tubular member 160 may be disposed distal of the tapered portion 144 of the second portion 140 of the metallic tubular member 120. In some embodiments, heat may be applied to the proximal end of the polymeric tubular member 160 before and/or during insertion of the flaring mandrel to widen the proximal end of the polymeric tubular member 160. In some embodiments, the flaring mandrel may be heated. In some embodiments, the polymeric tubular member 160 may be advanced proximally over the distal portion of the polymeric sheath 150 and the distal portion 146 of the second portion 140 of the metallic tubular member 120.

In some embodiments, the polymeric tubular member 160 may include a proximal portion 162 (e.g., FIG. 8) comprising a first polymeric material and a distal portion 164 (e.g., FIG. 8) comprising a second polymeric material. In at least some embodiments, the first polymeric material may be different from the second polymeric material. In some embodiments, the proximal portion 162 and the distal portion 164 may be bonded, melted, comingled, co-extruded, reflowed, or otherwise permanently joined together to render the polymeric tubular member 160 as a single unitary and/or monolithic structure. In some embodiments, the first polymeric material may be a polyimide 12, such as VESTAMID® L, and the second polymeric material may be a polyether block amide, such as PEBAX®. In one example, the first polymeric material may be VESTAMID® L2101F and the second polymeric material may be PEBAX® 63D. Other materials and/or combinations of materials are also contemplated. In at least some embodiments, the second polymeric material may be softer and/or more flexible than the first polymeric material.

In some embodiments, the polymeric tubular member 160 may have an overall length of about 15 centimeters (cm), about 20 cm, about 24 cm, about 26 cm, about 26.5 cm, about 27 cm, about 30 cm, about 35 cm, or another suitable overall length depending upon the intended procedure. In one example, the proximal portion 162 may have a length of about 22 cm and the distal portion 164 may have a length of about 4.5 cm. In other examples, the proximal portion 162 may have a length of about 10 cm to about 30 cm and the distal portion 164 may have a length of about 3 cm to about 6 cm. In some embodiments, the polymeric tubular member 160 may have a substantially uniform outer diameter and/or a substantially uniform inner diameter throughout its entire length, including the proximal portion 162 and the distal portion 164. However, other configurations, including but not limited to tapered and/or stepped configurations, are also contemplated. In one example, the polymeric tubular member 160 may have an outer diameter of about 0.021 inches (about 0.5334 millimeters). In other examples, the polymeric tubular member 160 may have an outer diameter of about 0.018 inches (about 0.4572 millimeters) to about 0.024 inches (about 0.6096 millimeters). In one example, the polymeric tubular member 160 may have an inner diameter of about 0.015 inches (about 0.381 millimeters). In other examples, the polymeric tubular member 160 may have an outer diameter of about 0.012 inches (about 0.3048 millimeters) to about 0.018 inches (about 0.4572 millimeters).

In at least some embodiments, the polymeric tubular member 160 may include a radiopaque marker band 166 (e.g., FIGS. 8-9) disposed within the distal portion 164 of the polymeric tubular member 160 and/or proximate the junction between the proximal portion 162 and the distal portion 164. In some embodiments, the radiopaque marker band 166 may be embedded within a wall of the polymeric tubular member 160. In some embodiments, the radiopaque marker band 166 may be secured within the lumen of the polymeric tubular member 160 such as with adhesive, friction fit, and/or interference fit. Some suitable materials for the radiopaque marker band 166 are discussed below.

Figure 5:
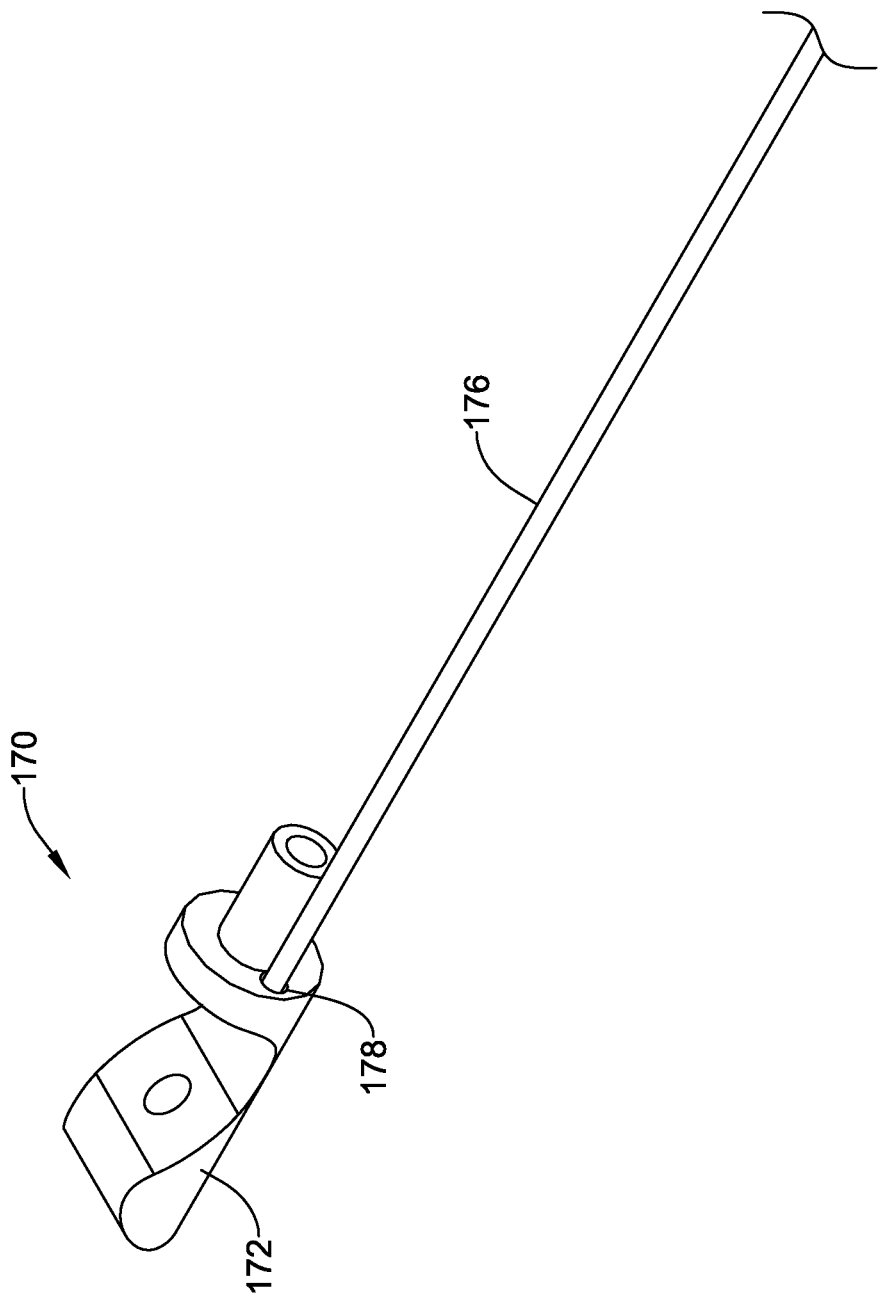

The method of manufacturing the elongate shaft 110 may include fixedly attaching the proximal coupler 172 of the release mechanism 170 to a distal end of a longitudinal support filament 176, as seen in FIG. 5. In at least some embodiments, the proximal coupler 172 of the release mechanism 170 may include an aperture 178 formed in a proximal portion thereof, the aperture 178 being configured to receive the distal end of the longitudinal support filament 176 therein. The distal end of the longitudinal support filament 176 may be fixedly attached to the proximal coupler 172 of the release mechanism 170 by, for example but not limited to adhesive bonding, welding, brazing, interference fit, friction fit, etc. as long as the resulting attachment is permanent.

In at least some embodiments, the longitudinal support filament 176 may be a metallic wire. In some embodiments, the longitudinal support filament 176 may have a substantially uniform outer diameter along its entire length. In one example, the longitudinal support filament 176 may have an outer diameter of about 0.0025 inches (about 0.0635 millimeters). In other examples, the longitudinal support filament 176 may have an outer diameter of about 0.0015 inches (about 0.0381 millimeters) to about 0.0035 inches (about 0.0889 millimeters). In one example, the longitudinal support filament 176 may be a tungsten-based alloy, or a nickel-cobalt or cobalt based alloy, such as 35N LT®. In some embodiments, the longitudinal support filament 176 may be capable of welding to and/or with platinum-iridium alloys. In some embodiments, the proximal coupler 172 and/or the distal coupler 174 may be formed from a platinum-iridium alloy. In some embodiments, the longitudinal support filament 176 resists corrosion with and/or when in contact with platinum-iridium alloys and nickel-titanium alloys. The longitudinal support filament 176 may have a high modulus of elasticity (e.g., greater than $33 \times 10^6$ pounds per square inch or 233 gigapascals) for stretch resistance, thereby allowing a smaller wire diameter to be used while achieving acceptable resistance to axial stretch and bending/flexibility characteristics. Other materials are also contemplated.

Figure 6:
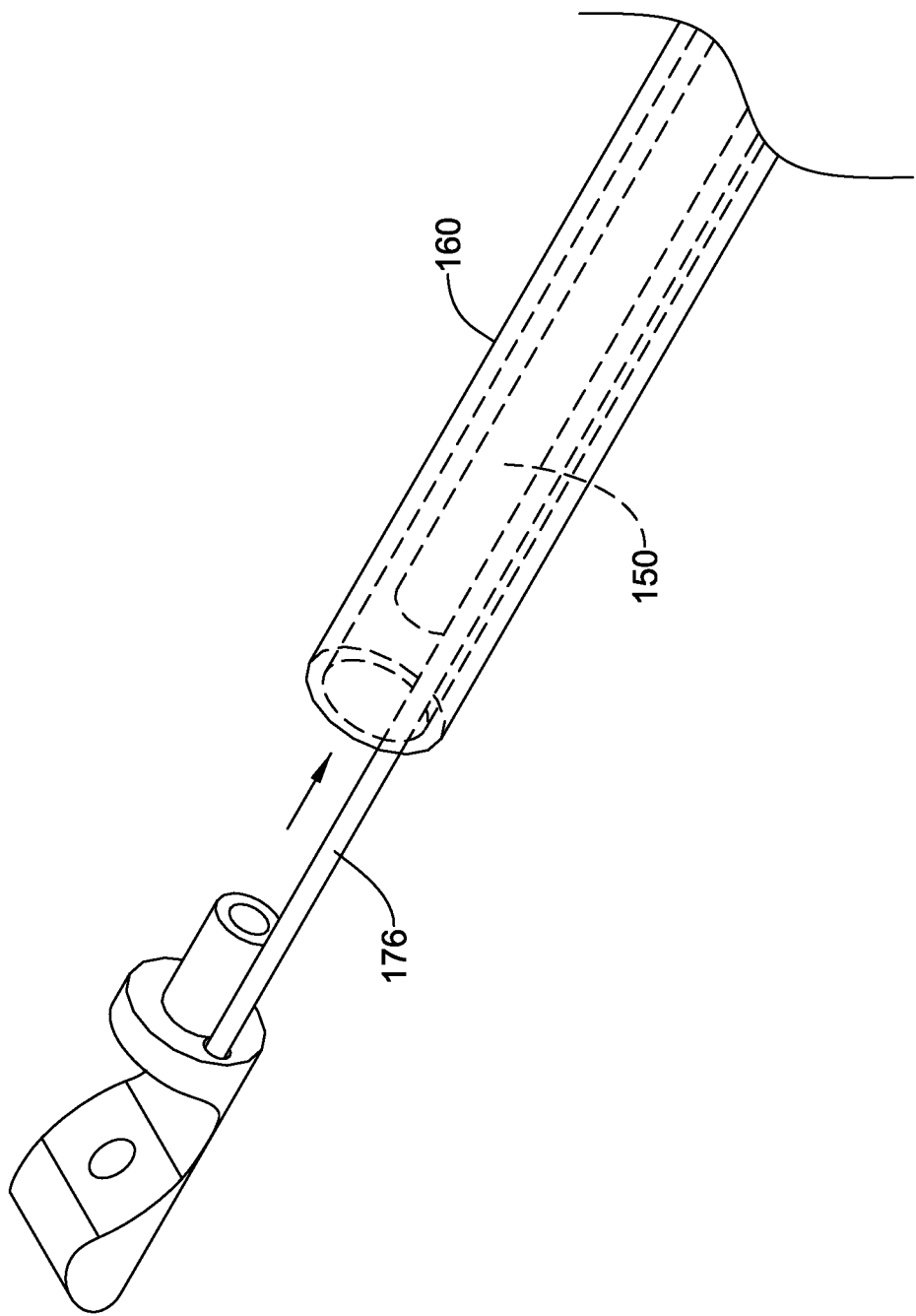

As shown in FIG. 6, the method may include inserting a proximal end of the longitudinal support filament 176 between the polymeric sheath 150 and the polymeric tubular member 160 proximate the distal ends of the polymeric sheath 150 and the polymeric tubular member 160 to position the longitudinal support filament 176 alongside the distal portion 146 of the second portion 140 of the metallic tubular member 120 (e.g., FIGS. 8 and 9) and the distal portion of the polymeric sheath 150. Inserting the proximal end of the longitudinal support filament 176 between the polymeric sheath 150 and the polymeric tubular member 160 may include advancing the proximal end of the longitudinal support filament 176 proximally between the polymeric sheath 150 and the polymeric tubular member 160 until the proximal end of the longitudinal support filament 176 axially overlaps and is positioned radially outward of the distal portion 146 of the second portion 140 of the metallic tubular member 120 (e.g., FIGS. 8 and 9). In some embodiments, the longitudinal support filament 176 may be oriented substantially parallel to the central longitudinal axis of the elongate shaft 110.

Figure 7:
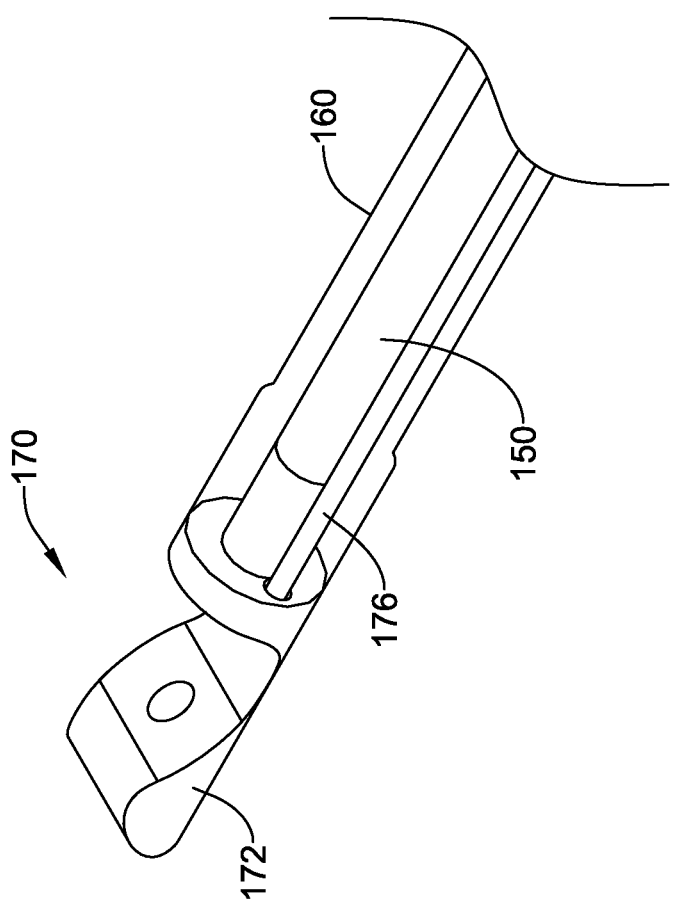
Figure 8:
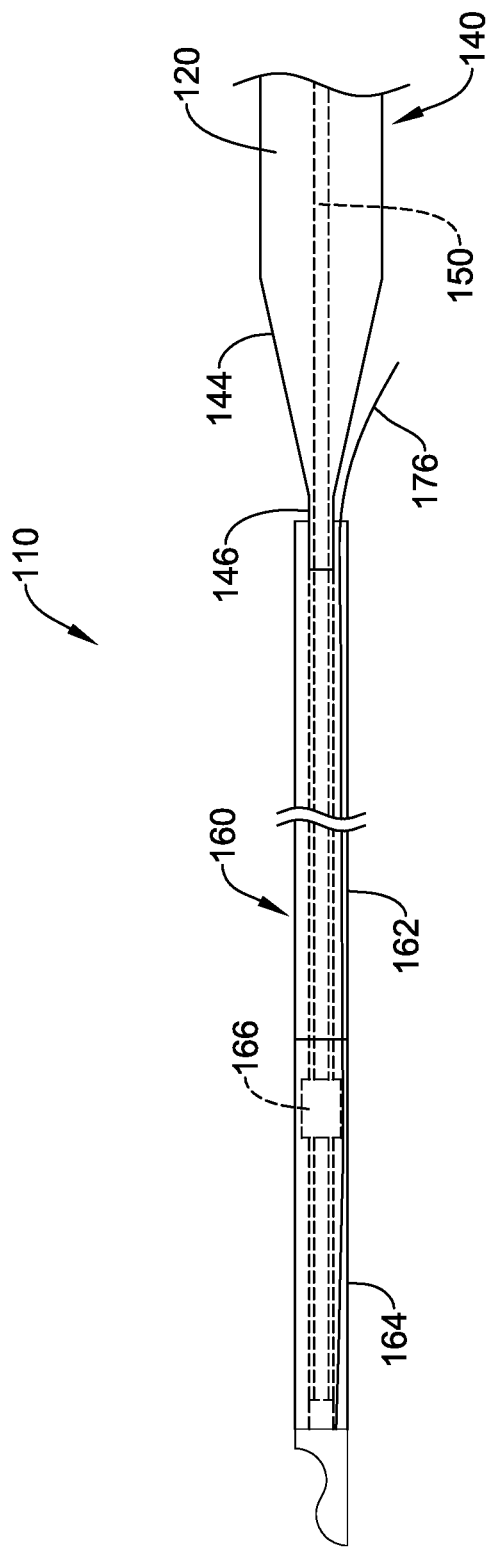

In some embodiments, after inserting the longitudinal support filament 176 between the polymeric sheath 150 and the polymeric tubular member 160 (and/or before reflowing the polymeric tubular member 160, as discussed herein), the method may include engaging and/or abutting a proximal end and/or a proximal face of the proximal coupler 172 of the release mechanism 170 with and/or against the distal end of the polymeric sheath 150, as shown in partial cutaway in FIG. 7. In some embodiments, after inserting the longitudinal support filament 176 between the polymeric sheath 150 and the polymeric tubular member 160 (and/or before reflowing the polymeric tubular member 160, as discussed herein), the proximal portion of the longitudinal support filament 176 may extend proximal of the distal portion 146 of the second portion 140 of the metallic tubular member 120 and/or alongside the tapered portion 144 of the second portion 140 of the metallic tubular member 120, as shown in FIG. 8. In FIG. 8, the longitudinal support filament 176 is shown as a solid line merely for illustrative and clarity purposes. As discussed above, in at least some embodiments, the polymeric tubular member 160 may include the radiopaque marker band 166, as seen in FIGS. 8 and 9.

Figure 9:
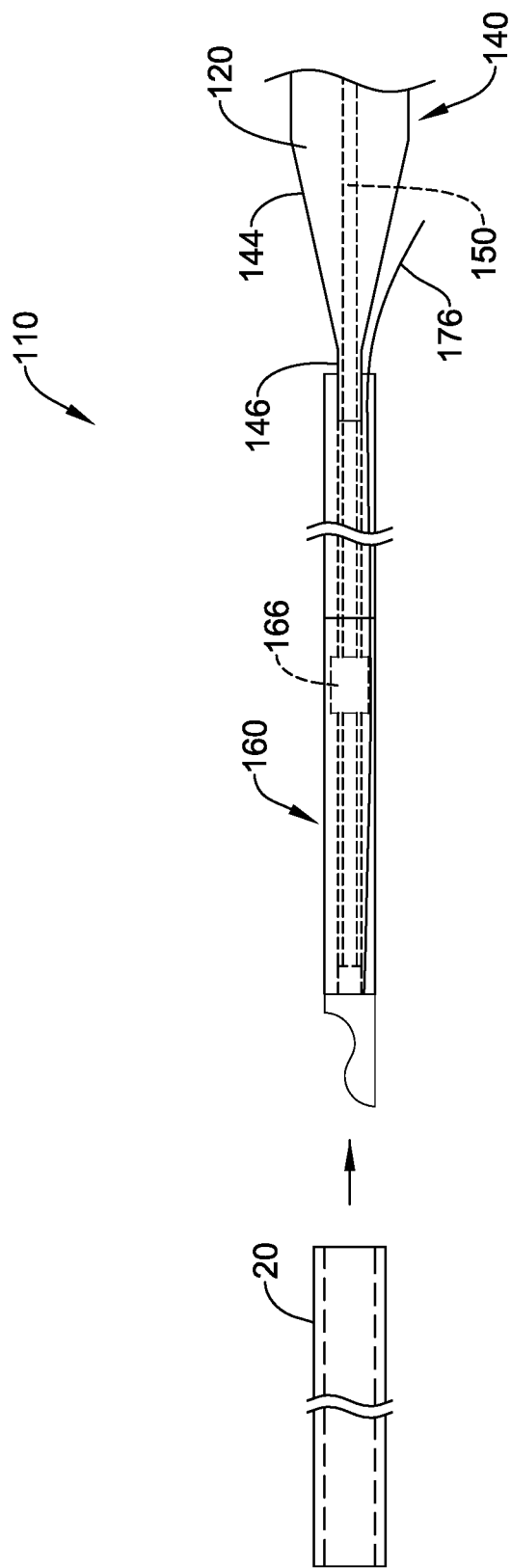
Figure 10:
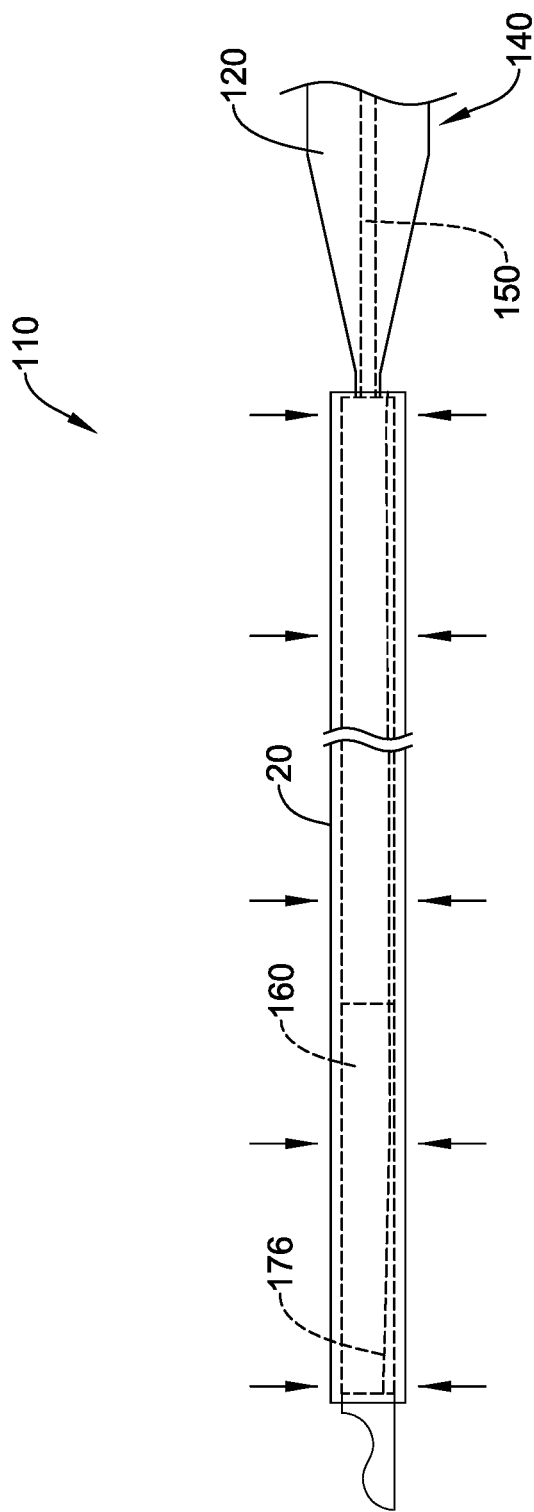

FIG. 9 illustrates that in some embodiments, after inserting the longitudinal support filament 176 between the polymeric sheath 150 and the polymeric tubular member 160 (and/or before reflowing the polymeric tubular member 160, as discussed herein), the method may include positioning a tubular heat shrink member 20 over the polymeric tubular member 160. In FIG. 9, the longitudinal support filament 176 is shown as a solid line merely for illustrative and clarity purposes. The method may include reflowing the polymeric tubular member 160 to secure the longitudinal support filament 176 relative to the polymeric sheath 150 and the metallic tubular member 120, as shown in FIG. 10. Reflowing the polymeric tubular member 160 may include applying heat to the tubular heat shrink member 20 and the polymeric tubular member 160 disposed therein. The tubular heat shrink member 20 may be configured to return to a smaller diameter upon exposure to sufficient heat, thereby applying radially inward pressure upon the polymeric tubular member 160 as the heat softens and/or melts the polymeric tubular member 160, thereby causing reflow of the polymeric tubular member 160 around the polymeric sheath 150, the radiopaque marker band 166, the longitudinal support filament 176, and the distal portion 146 of the second portion 140 of the metallic tubular member 120. The method may further include, before reflowing the polymeric tubular member 160, trimming the longitudinal support filament 176 proximate the proximal end of the polymeric tubular member 160, as seen in FIG. 10.

Figure 11:
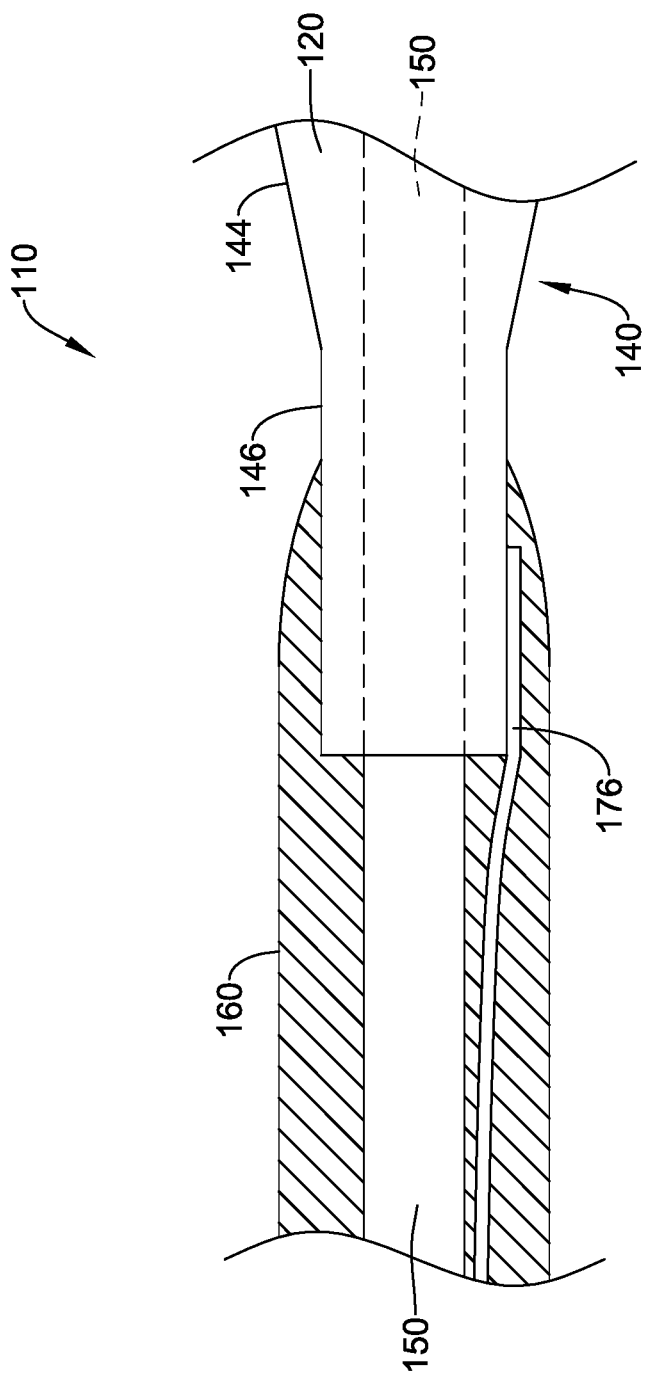

In some examples, after reflowing the polymeric tubular member 160, the tubular heat shrink member 20 may be removed from the elongate shaft 110. In some examples, after reflowing the polymeric tubular member 160, a distal portion of the longitudinal support filament 176 is positioned directly against the outer surface of the distal portion of the polymeric sheath 150. In some examples, after reflowing the polymeric tubular member 160, a proximal portion of the longitudinal support filament 176 is positioned directly against an outer surface of the distal portion 146 of the second portion 140 of the metallic tubular member 120, as seen in FIG. 11. In some examples, after reflowing the polymeric tubular member 160, a proximal-most end of the polymeric tubular member 160 is disposed distal of the distally tapered portion 144 of the second portion 140 of the metallic tubular member 120. In some examples, after reflowing the polymeric tubular member 160, the proximal-most end of the polymeric tubular member 160 may be rounded toward the distal portion 146 of the second portion 140 of the metallic tubular member 120. In some examples, after reflowing the polymeric tubular member 160, the proximal-most end of the polymeric tubular member 160 extends proximal of a proximal end of the longitudinal support filament 176, as seen in FIG. 11. In some examples, after reflowing the polymeric tubular member 160, the proximal end of the polymeric tubular member 160 may pinch or squeeze the proximal end of the longitudinal support filament 176 against the distal portion 146 of the second portion 140 of the metallic tubular member 120.

Figure 12:
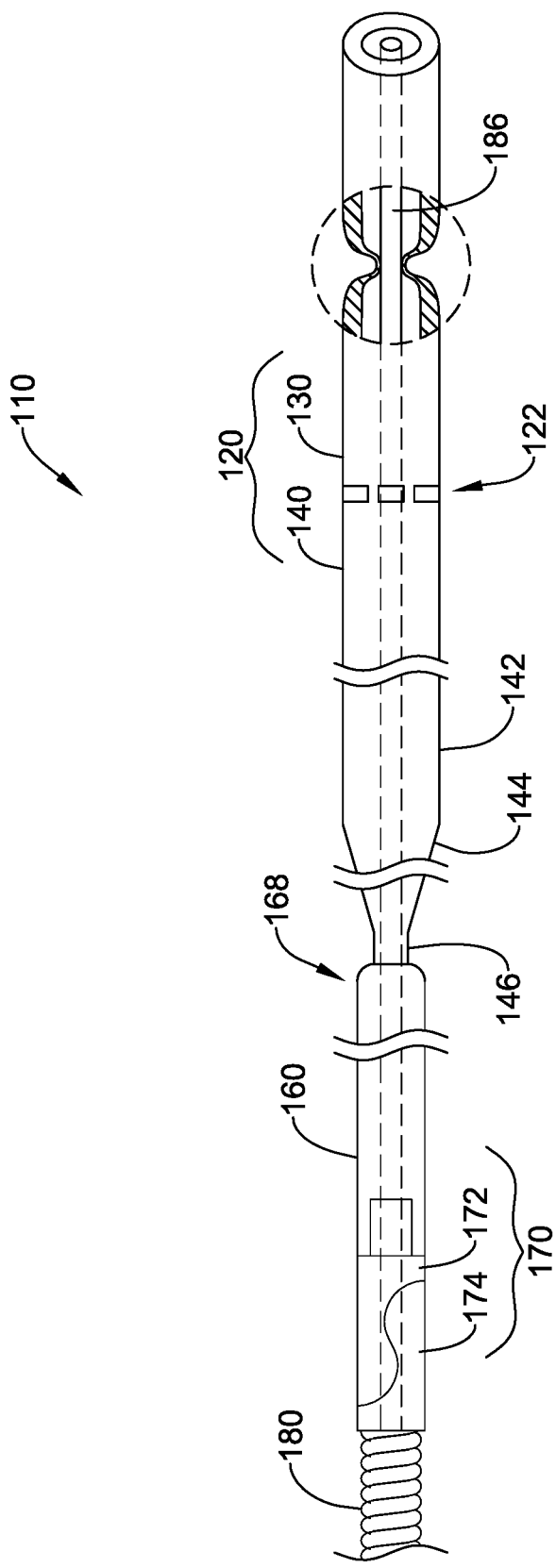

In some examples, after reflowing the polymeric tubular member 160, the method may include applying a hydrophobic coating 168 to the outer surface of the polymeric tubular member 160 and/or to exposed portions of the outer surface of the metallic tubular member 120. In some embodiments, after reflowing the polymeric tubular member 160, the method may include removing the mandrel 10 from the lumen of the polymeric sheath 150. Thereafter, the method may include disposing a release wire 186 axially within the lumen of the polymeric sheath 150, and through the proximal coupler 172 and the distal coupler 174 to releasably couple the medical device 180 to the proximal coupler 172 and/or the elongate shaft 110, as shown in FIG. 12. In some embodiments, the release wire 186 may be a metallic wire with limited axial stretching capability. Some suitable but non-limiting materials for the release wire 186 are described below. In some embodiments, disposing the release wire 186 within the lumen of the polymeric sheath 150 may include inserting a distal end of the release wire 186 into a proximal end of the polymeric sheath 150 and/or a proximal end of the metallic tubular member 120, advancing the distal end of the release wire 186 distally within the lumen of the polymeric sheath 150, through the proximal coupler 172, and into engagement with and/or into the distal coupler 174.

Thereafter, the method may include crimping or swaging the first portion 130 of the metallic tubular member 120 onto the release wire 186 to fixedly secure the release wire 186 to the first portion 130 of the metallic tubular member 120, as seen in partial cutaway in FIG. 12. Crimping or swaging the first portion 130 of the metallic tubular member 120 onto the release wire 186 may include forcing an inner surface of the wall of the metallic tubular member 120 into contact with the outer surface of the release wire 186. In some embodiments, crimping or swaging the first portion 130 of the metallic tubular member 120 onto the release wire 186 may include reducing the outer diameter of the release wire 186 within a crimped area to create a mechanical interlock between the metallic tubular member 120 and the release wire 186.

In some examples, the first portion 130 of the metallic tubular member 120 may be disposed proximal of the pre-defined break region 122 and the second portion 140 of the metallic tubular member 120 may be disposed distal of the pre-defined break region 122. In some examples, the first portion 130 of the metallic tubular member 120 may be integrally formed with the second portion 140 of the metallic tubular member 120 as a unitary and/or monolithic structure. The pre-defined break region 122 may be formed in the wall of the metallic tubular member 120. In some examples, the pre-defined break region 122 may include a plurality of slits and/or notches formed in the wall of the metallic tubular member 120. Other configurations are contemplated. For example, the pre-defined break region 122 may include a perforation, a plurality of apertures extending through the wall of the metallic tubular member 120, a thinned or weakened feature or features formed in the wall of the metallic tubular member 120, etc. The first portion 130 of the metallic tubular member 120 may be configured to disengage from the second portion 140 of the metallic tubular member 120 at the pre-defined break region 122. However, regardless of form, the pre-defined break region 122 may generally be strong enough to avoid and/or prevent accidental or unintended disengagement of the first portion 130 of the metallic tubular member 120 from the second portion 140 of the metallic tubular member 120 in normal use and/or handling of the medical device system and/or the elongate shaft 110.

As seen in FIG. 12, the medical device system may include the release wire 186 disposed within the lumen of the metallic tubular member 120, the polymeric sheath 150 (not shown), and/or the elongate shaft 110. The release wire 186 may be configured to releasably attach the medical device 180 to the distal end of the elongate shaft 110 in a first position, as seen in FIG. 12 for example. In some embodiments, the release wire 186 may be alternately and/or interchangeably referred to as a pull wire, an actuation wire, and/or a locking wire. The release wire 186 may generally be a solid wire or shaft but may also be tubular in some embodiments. As discussed herein, the first portion 130 of the metallic tubular member 120 may be fixedly attached to a proximal portion of the release wire 186 proximal of the pre-defined break region 122.

In use, the microcatheter 190 (e.g., FIG. 1) of the medical device system may be inserted into a patient's anatomy and a distal end thereof guided and/or advanced to a location adjacent a treatment site. The medical device 180 disposed at the distal end of the elongate shaft 110 may be advanced through the microcatheter 190 to the treatment site. In some embodiments, the medical device 180 may be disposed within the lumen of the microcatheter 190 proximate to the distal end of the elongate shaft 110. In some embodiments, the medical device 180 may be disposed within the lumen of the microcatheter 190 proximate to the distal end of the elongate shaft 110 prior to use and/or prior to inserting the microcatheter 190 into the patient's anatomy. Deployment and/or release of the medical device 180 may be performed selectively depending upon the type of medical device and/or the desired treatment process or method. The elongate shaft 110 may have sufficient length that the proximal end of the elongate shaft 110 remains proximal of (e.g., extend proximally from) the microcatheter 190 when the medical device 180 is disposed distal of the microcatheter 190. In use, the elongate shaft 110 may have sufficient length to reach from the treatment site to a position outside of the patient where the medical device system may be manipulated by the user.

When the user is ready to detach and/or release the medical device 180 from the elongate shaft 110 (e.g., when the medical device 180 has been positioned at the target site), the user may hold the second portion 140 of the metallic tubular member 120 to prevent movement of the second portion 140 of the metallic tubular member 120 and the user may bend the first portion 130 of the metallic tubular member 120 relative to the second portion 140 of the metallic tubular member 120 to thereby apply a moment around the pre-defined break region 122. This moment may cause a break to form in the metallic tubular member 120 at the pre-defined break region 122, thereby disengaging the first portion 130 of the metallic tubular member 120 from the second portion 140 of the metallic tubular member 120.

Disengaging the first portion 130 of the metallic tubular member 120 from the second portion 140 of the metallic tubular member 120 permits the release wire 186 to axially translate and/or move relative to a distal portion of the elongate shaft 110, the release mechanism 170, and/or the medical device 180. As such, the release wire 186 is translatable and/or movable to a second position when the second portion 140 of the metallic tubular member 120 is disengaged from the first portion 130 of the metallic tubular member 120. With the release wire 186 in the second position, the medical device 180 may be detachable from the proximal coupler 172 of the release mechanism 170 and/or the distal end of the elongate shaft 110. Accordingly, axial and/or proximal translation and/or movement of the first portion 130 of the metallic tubular member 120 relative to the second portion 140 of the metallic tubular member 120 may proximally retract the release wire 186 to the second position, thereby releasing the distal coupler 174 of the release mechanism 170 and/or the medical device 180 from the proximal coupler 172 of the release mechanism 170 and/or the distal end of the elongate shaft 110.

FIGS. 13-17 illustrate aspects of another example method of manufacturing an elongate shaft for delivering the medical device 180. While the method refers to an elongate shaft 210 (e.g., FIGS. 15-16), it shall be understood that the elongate shaft 210 may be used and/or referred to interchangeably with the elongate shaft 110 in the medical device system. Components and/or elements independent of the construction of the elongate shaft (e.g., the medical device 180, the microcatheter 190, etc.) may be the same as those described above, and not all elements are shown in each figure. Similarly, some of the same components and/or elements used in constructing the elongate shaft 110 (e.g., the release mechanism 170, the release wire 186, etc.) may also be used in construction of the elongate shaft 210, and thus the same reference numbers are used and the description of those elements is not repeated in the interest of brevity.

Figure 13:
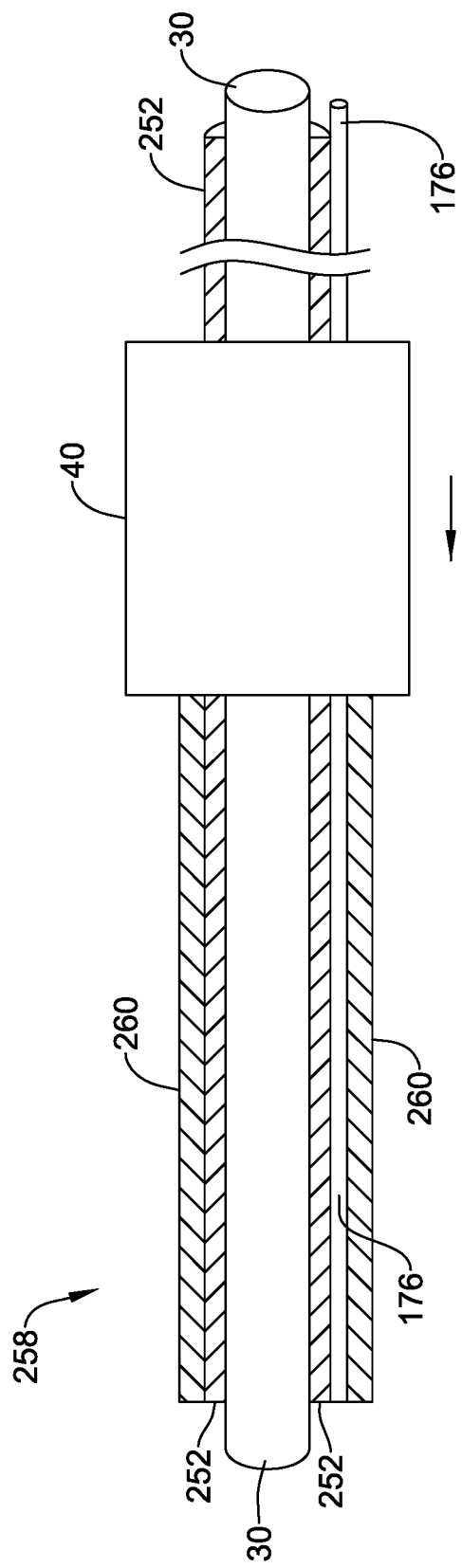
FIGS. 13-17 illustrate aspects of a method of manufacturing a delivery shaft.

As shown in FIG. 13, the method may include extruding a polymeric tubular member 260 and a longitudinal support filament 176 over a first polymeric sheath 252 disposed on a mandrel 30 to form a composite tubular member 258. In some embodiments, as may be seen in FIG. 13, the longitudinal support filament 176 may be fed through an extrusion machine 40 alongside the first polymeric sheath 252 disposed on the mandrel 30. In some embodiments, the longitudinal support filament 176 may be extruded at the same time as the polymeric tubular member 260 and/or may be co-extruded with the polymeric tubular member 260.

In some embodiments, the first polymeric sheath 252 may be formed directly on the mandrel 30. For example, the first polymeric sheath 252 may be extruded onto the mandrel 30. In another example, the first polymeric sheath 252 may be formed as a tubular structure and the mandrel 30 may be inserted into the first polymeric sheath 252 (or the first polymeric sheath 252 may be slid over the mandrel 30). In one example, the first polymeric sheath 252 may have an outer diameter of about 0.006 inches (about 0.1524 millimeters). In other examples, the first polymeric sheath 252 may have an outer diameter of about 0.004 inches (0.1016 millimeters) to about 0.008 inches (about 0.2032 millimeters). The mandrel 30 may be removable from the first polymeric sheath 252, as discussed herein. In some embodiments, the mandrel 30 may be slidable with respect to the first polymeric sheath 252. In some embodiments, the first polymeric sheath 252 may have a slight friction fit and/or a slight interference fit with the mandrel 30 (e.g., the mandrel 30 may not move freely relative to the first polymeric sheath 252) that may be overcome at a later time to remove the mandrel 30 from the lumen of the first polymeric sheath 252. In one example, the first polymeric sheath 252 may be formed from polytetrafluoroethylene (PTFE). Other materials are also contemplated. In at least some embodiments, an outer surface of the first polymeric sheath 252 may be etched and/or otherwise mechanically or chemically treated to facilitate bonding and/or securement to another material.

In some embodiments, the polymeric tubular member 260 may include a proximal portion comprising a first polymeric material and a distal portion comprising a second polymeric material. In at least some embodiments, the first polymeric material may be different from the second polymeric material. In some embodiments, the proximal portion and the distal portion may be bonded, melted, comingled, co-extruded, reflowed, or otherwise permanently joined together to render the polymeric tubular member as a single unitary and/or monolithic structure. In some embodiments, the first polymeric material may be a polyimide 12, such as VESTA-MID® L, and the second polymeric material may be a polyether block amide, such as PEBAX®. In one example, the first polymeric material may be VESTAMID® L2101F and the second polymeric material may be PEBAX® 63D. Other materials and/or combinations of materials are also contemplated. In at least some embodiments, the second polymeric material may be softer and/or more flexible than the first polymeric material.

In some embodiments, the polymeric tubular member 260 may have an overall length of about 15 centimeters (cm), about 20 cm, about 24 cm, about 26 cm, about 26.5 cm, about 27 cm, about 30 cm, about 35 cm, or another suitable overall length depending upon the intended procedure. In one example, the proximal portion may have a length of about 22 cm and the distal portion may have a length of about 4.5 cm. In other examples, the proximal portion may have a length of about 10 cm to about 30 cm and the distal portion may have a length of about 3 cm to about 6 cm. In some embodiments, the polymeric tubular member 260 may have a substantially uniform outer diameter and/or a substantially uniform inner diameter throughout its entire length, including the proximal portion and the distal portion. However, other configurations, including but not limited to tapered and/or stepped configurations, are also contemplated. In one example, the polymeric tubular member 260 may have an outer diameter of about 0.016 inches (about 0.4064 millimeters). In other examples, the polymeric tubular member 160 may have an outer diameter of about 0.014 inches (about 0.3556 millimeters) to about 0.018 inches (about 0.4572 millimeters).

In at least some embodiments, the polymeric tubular member 260 may include a radiopaque marker band disposed within the distal portion of the polymeric tubular member 260 and/or proximate the junction between the proximal portion and the distal portion. In some embodiments, the radiopaque marker band may be fed through the extrusion machine 40 over the first polymeric sheath 252 and the longitudinal support filament 176 during formation of the composite tubular member 258 to embed the radiopaque marker within a wall of the polymeric tubular member 260 and/or the composite tubular member 258. In some embodiments, the radiopaque marker may be secured to an outer surface of the polymeric tubular member 260. In some embodiments, the radiopaque marker may be secured to the outer surface of the distal portion of the polymeric tubular member 260. In some embodiments, the radiopaque marker may be secured to the outer surface of the polymeric tubular member 260 adjacent to and/or at the junction between the proximal portion and the distal portion of the polymeric tubular member 260. In some embodiments, the radiopaque marker may be fixedly secured to the outer surface of the polymeric tubular member 260. For example, the radiopaque marker may be adhesively bonded to the outer surface of the polymeric tubular member 260, crimped and/or swaged onto the outer surface of the polymeric tubular member 260, and/or fixedly secured to the outer surface of the polymeric tubular member 260 using a heat shrink element. Other configurations and/or methods of adding a radiopaque marker to the composite tubular member 258 are also contemplated.

In some examples, after extruding the polymeric tubular member 260 over the first polymeric sheath 252 and/or after forming the composite tubular member 258, the polymeric tubular member 260 may be fixedly and permanently attached (e.g., bonded, comingled, coextruded, etc.) to the first polymeric sheath 252. In some examples, after extruding the polymeric tubular member 260 over the first polymeric sheath 252 and/or after forming the composite tubular member 258, the longitudinal support filament 176 may be embedded within and/or surrounded by the polymeric tubular member 260 and/or the composite tubular member 258. In some examples, after extruding the polymeric tubular member 260 over the first polymeric sheath 252 and/or after forming the composite tubular member 258, the longitudinal support filament 176 may be positioned in direct contact with the first polymeric sheath 252 and/or the polymeric tubular member 260.

Figure 14:
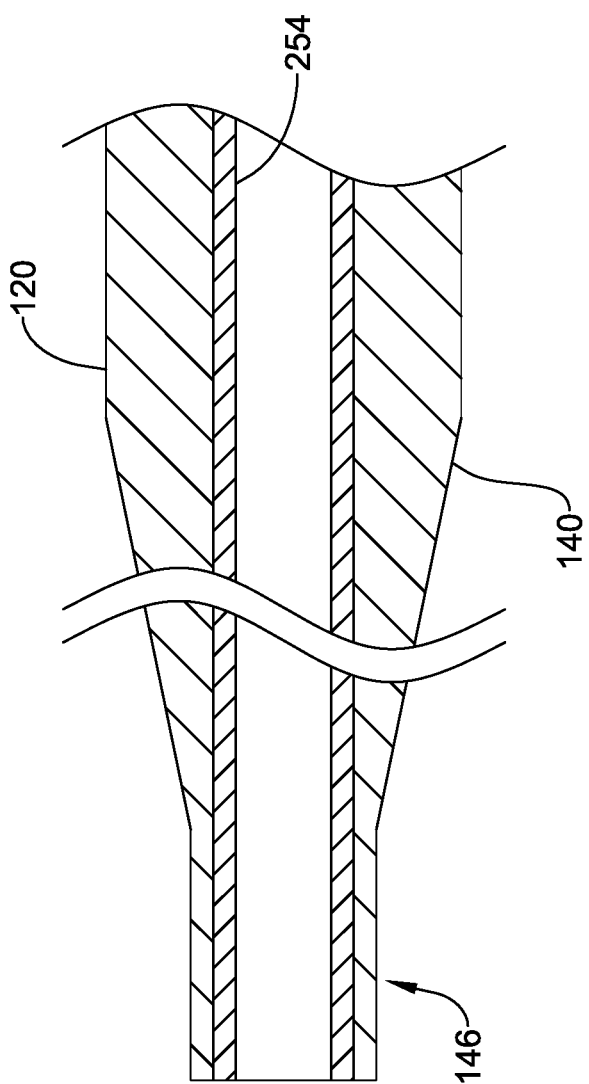

The method may include sliding a metallic tubular member 120 over a second polymeric sheath 254 or sliding the second polymeric sheath 254 into a lumen of the metallic tubular member 120. In one example, the second polymeric sheath 254 may have an outer diameter of about 0.006 inches (about 0.1524 millimeters). In other examples, the second polymeric sheath 254 may have an outer diameter of about 0.004 inches (0.1016 millimeters) to about 0.008 inches (about 0.2032 millimeters). In one example, the second polymeric sheath 254 may be formed from polytetrafluoroethylene (PTFE). Other materials are also contemplated. In at least some embodiments, an outer surface of the second polymeric sheath 254 may be etched and/or otherwise mechanically or chemically treated to facilitate bonding and/or securement to another material. In some embodiments, the second polymeric sheath 254 may be formed and/or inserted using a mandrel, similar to the first polymeric sheath 252 above. The metallic tubular member 120 may be the same metallic tubular member 120 used and described above, and thus the physical characteristics of the metallic tubular member 120 are not repeated. The method may include securing a distal end of the second polymeric sheath 254 to a distal end and/or to the distal portion 146 of the second portion 140 of the metallic tubular member 120, as shown in FIG. 14. In some embodiments, the method may further include trimming excess length off of the second polymeric sheath 254 such that a distal end of the second polymeric sheath 254 is coterminal with the distal end of the metallic tubular member 120.

Figure 15:
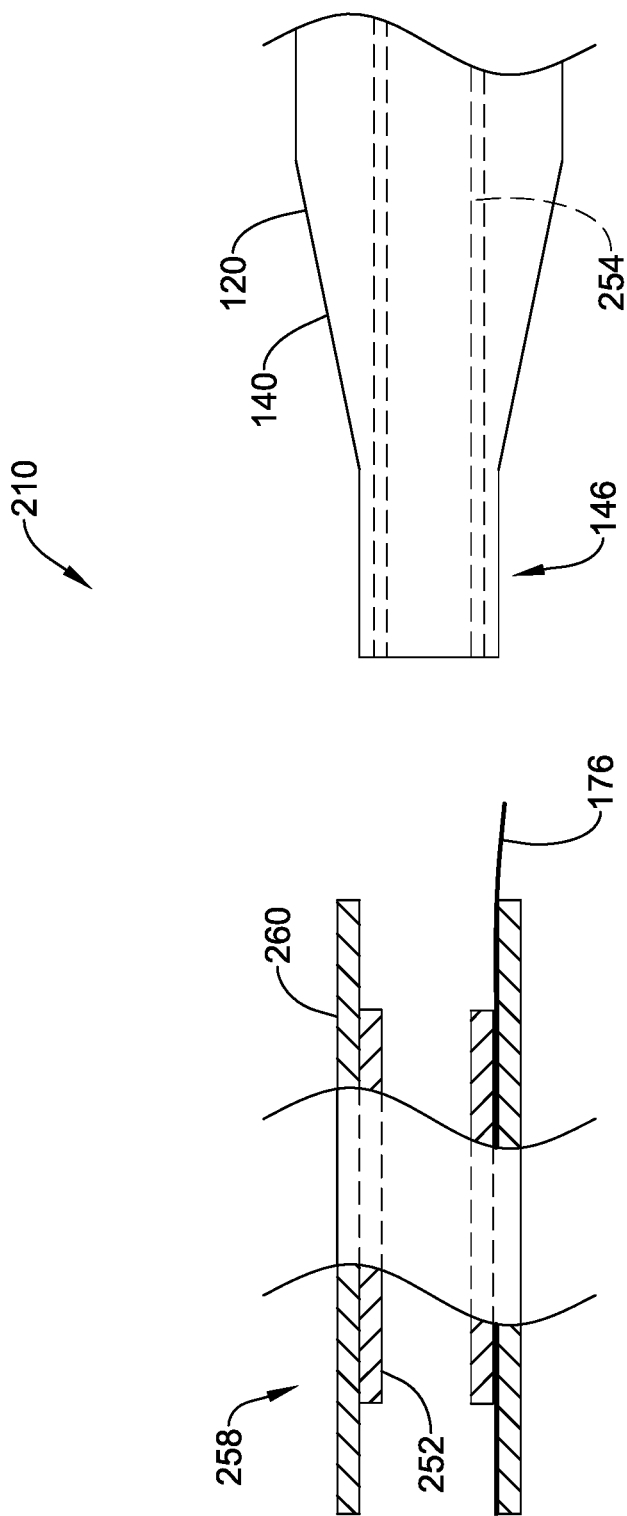

The method may include placing the composite tubular member 258, with the mandrel 30 removed, over the distal portion 146 of the second portion 140 of the metallic tubular member 120. In some embodiments, a proximal portion of the first polymeric sheath 252 may be removed from within the composite tubular member 258 before placing the composite tubular member 258 over the distal portion 146 of the second portion 140 of the metallic tubular member 120, as seen in FIG. 15. In some embodiments, a distal portion of the first polymeric sheath 252 is removed from within the composite tubular member 258 before placing the composite tubular member 258 over the distal portion 146 of the second portion 140 of the metallic tubular member 120. In some embodiments, the distal portion of the first polymeric sheath 252 is removed from within the composite tubular member 258 after placing the composite tubular member 258 over the distal portion 146 of the second portion 140 of the metallic tubular member 120.

In some examples, prior to placing the composite tubular member 258 over the distal portion 146 of the second portion 140 of the metallic tubular member 120, the longitudinal support filament 176 may extend proximal of the polymeric tubular member 260 and/or the first polymeric sheath 252. In some embodiments, the distal portion of the first polymeric sheath 252 is removed from within the composite tubular member 258, the longitudinal support filament 176 may extend distal of the first polymeric sheath 252.

Figure 16:
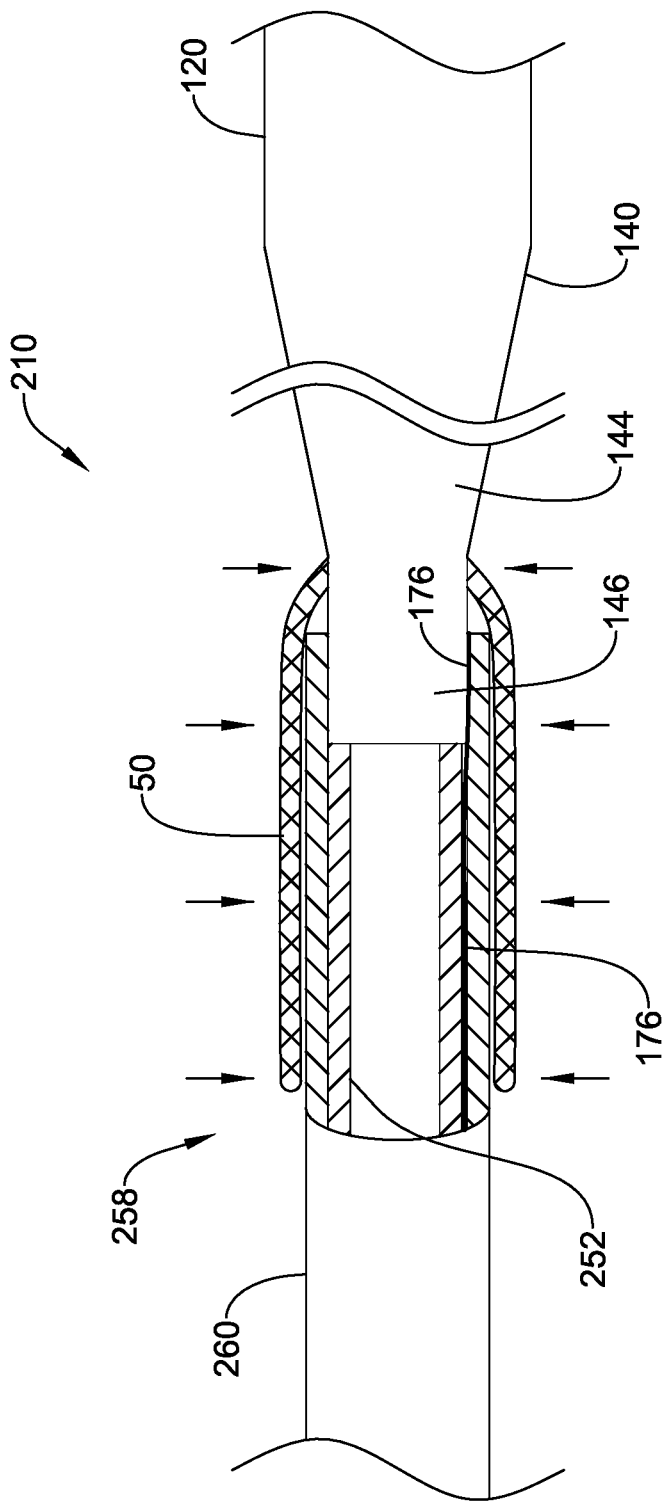

The method may include positioning a tubular heat shrink member 50 over a proximal portion of the polymeric tubular member 260 and at least a portion of the distal portion 146 of the second portion 140 of the metallic tubular member 120, as seen in FIG. 16. The method may include reflowing the proximal portion of the polymeric tubular member 260 of the composite tubular member 258 onto the distal portion 146 of the second portion 140 of the metallic tubular member 120 to secure the longitudinal support filament 176 relative to the metallic tubular member 120. In some embodiments, reflowing the polymeric tubular member 260 may include applying heat to the tubular heat shrink member 50 and the polymeric tubular member 260 disposed therein. The tubular heat shrink member 50 may be configured to return to a smaller diameter upon exposure to sufficient heat, thereby applying radially inward pressure upon the polymeric tubular member 260 as the heat softens and/or melts the polymeric tubular member 260, thereby causing reflow of the polymeric tubular member 260 around the first polymeric sheath 250, the longitudinal support filament 176, and the distal portion 146 of the second portion 140 of the metallic tubular member 120. The method may further include, before reflowing the polymeric tubular member 260, trimming the longitudinal support filament 176 proximate the proximal end of the polymeric tubular member 260. Reflowing the polymeric tubular member 260 may result in the structure shown in FIG. 11.

In some examples, after reflowing the proximal portion of the polymeric tubular member 260 (e.g., FIG. 16), the tubular heat shrink member 50 may be removed from the proximal portion of the polymeric tubular member 260. In some examples, after reflowing the proximal portion of the polymeric tubular member 260, a proximal portion of the longitudinal support filament 176 is positioned directly against an outer surface of the distal portion 146 of the second portion 140 of the metallic tubular member 120, resulting in a configuration similar to the configuration shown in FIG. 11. As such, reflowing the proximal portion of the polymeric tubular member 260 may secure the longitudinal support filament 176 against the outer surface of the distal portion 146 of the second portion 140 of the metallic tubular member 120. In some examples, after reflowing the proximal portion of the polymeric tubular member 260, a proximal-most end of the polymeric tubular member 260 is disposed distal of the distally tapered portion 144 of the second portion 140 of the metallic tubular member 120. In some examples, after reflowing the proximal portion of the polymeric tubular member 260, the proximal-most end of the polymeric tubular member 260 may be rounded toward the distal portion 146 of the second portion 140 of the metallic tubular member 120. In some embodiments, after reflowing the proximal portion of the polymeric tubular member 260, the proximal-most end of the polymeric tubular member 260 extends proximal of a proximal end of the longitudinal support filament 176. In some examples, after reflowing the proximal portion of the polymeric tubular member 260, the proximal end of the polymeric tubular member 260 may pinch or squeeze the proximal end of the longitudinal support filament 176 against the distal portion 146 of the second portion 140 of the metallic tubular member 120.

Figure 17:
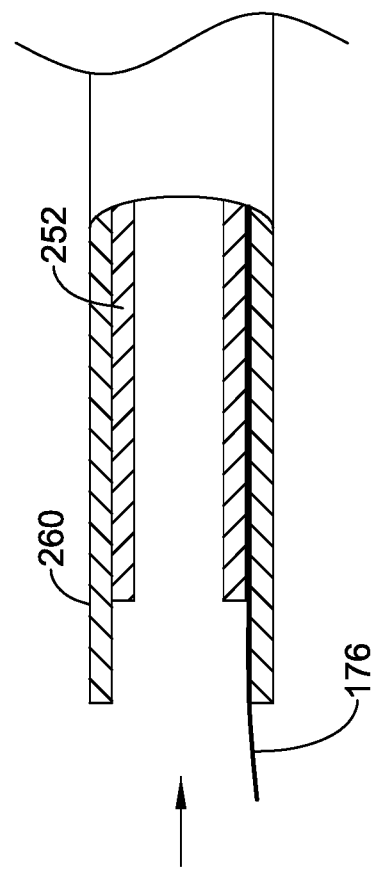
Figure 17:
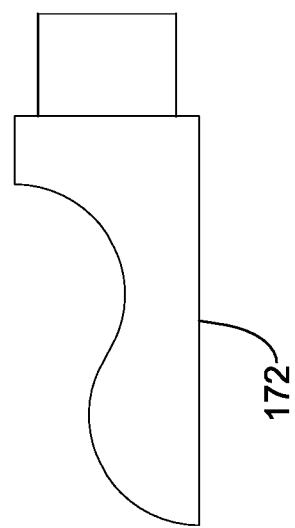

The method may further include fixedly attaching the proximal coupler 172 to the distal end of the longitudinal support filament 176. In at least some embodiments, a distal portion of the polymeric tubular member 260 may be removed to expose the distal end of the longitudinal support filament 176 prior to fixedly attaching the proximal coupler 172, as seen in FIG. 17. In some embodiments, prior to fixedly attaching the proximal coupler 172 to the distal end of the longitudinal support filament 176, the method may include trimming the distal end of the longitudinal support filament 176 such that the distal end of the longitudinal support filament 176 cannot extend distally through and/or from the proximal coupler 172. In some embodiments, after fixedly attaching the proximal coupler 172 to the distal end of the longitudinal support filament 176, the method may include trimming the distal end of the longitudinal support filament 176 such that the distal end of the longitudinal support filament 176 does not extend distally through and/or from the proximal coupler 172.

In some examples, after reflowing the proximal portion of the polymeric tubular member 260, the method may include applying a hydrophobic coating 168 to the outer surface of the polymeric tubular member 260 and/or to exposed portions of the outer surface of the metallic tubular member 120. Next, the method may include disposing a release wire 186 axially within the lumen of the first polymeric sheath 252 and the second polymeric sheath 254, and through the proximal coupler 172 and the distal coupler 174 to releasably couple the medical device 180 to the proximal coupler 172 and/or the elongate shaft 210, similar to the configuration shown in FIG. 12. In some examples, disposing the release wire 186 within the lumen of the first polymeric sheath 252 and the second polymeric sheath 254 may include inserting a distal end of the release wire 186 into a proximal end of the first polymeric sheath 252 and/or a proximal end of the metallic tubular member 120, advancing the distal end of the release wire 186 distally within the lumen of the first polymeric sheath 252 and the second polymeric sheath 254, through the proximal coupler 172, and into engagement with and/or into the distal coupler 174. Next, the method may include crimping or swaging the first portion 130 of the metallic tubular member 120 onto the release wire 186 to fixedly secure the release wire 186 to the first portion 130 of the metallic tubular member 120 as described above with respect to FIG. 12.

Figure 18:
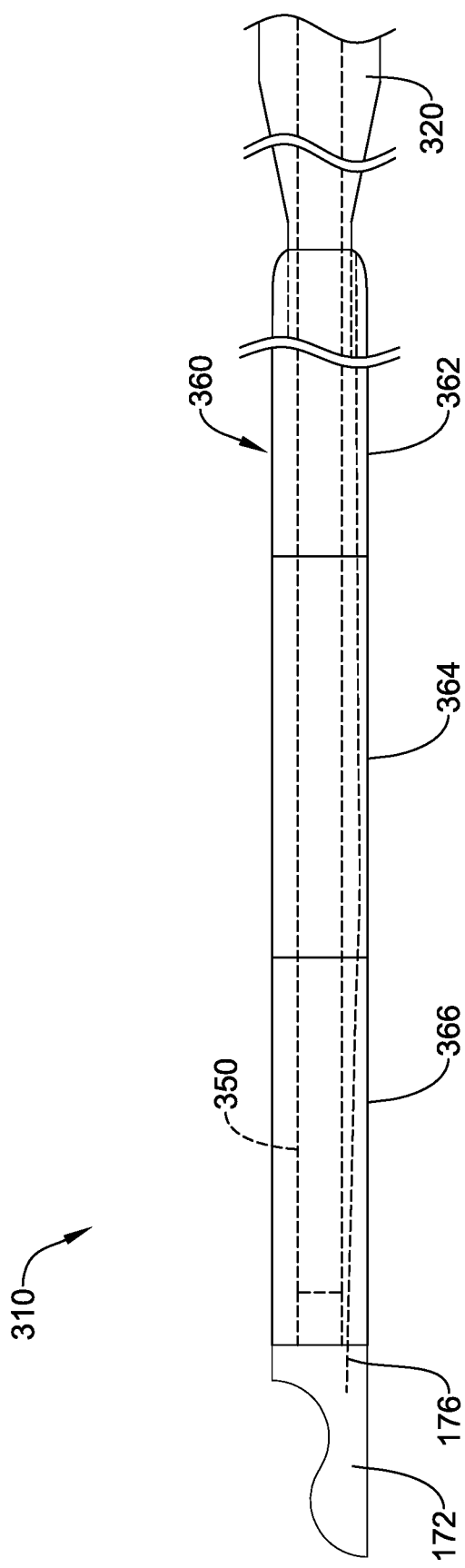
FIGS. 18-19 illustrate aspects of an alternative configuration for a delivery shaft.
Figure 19:
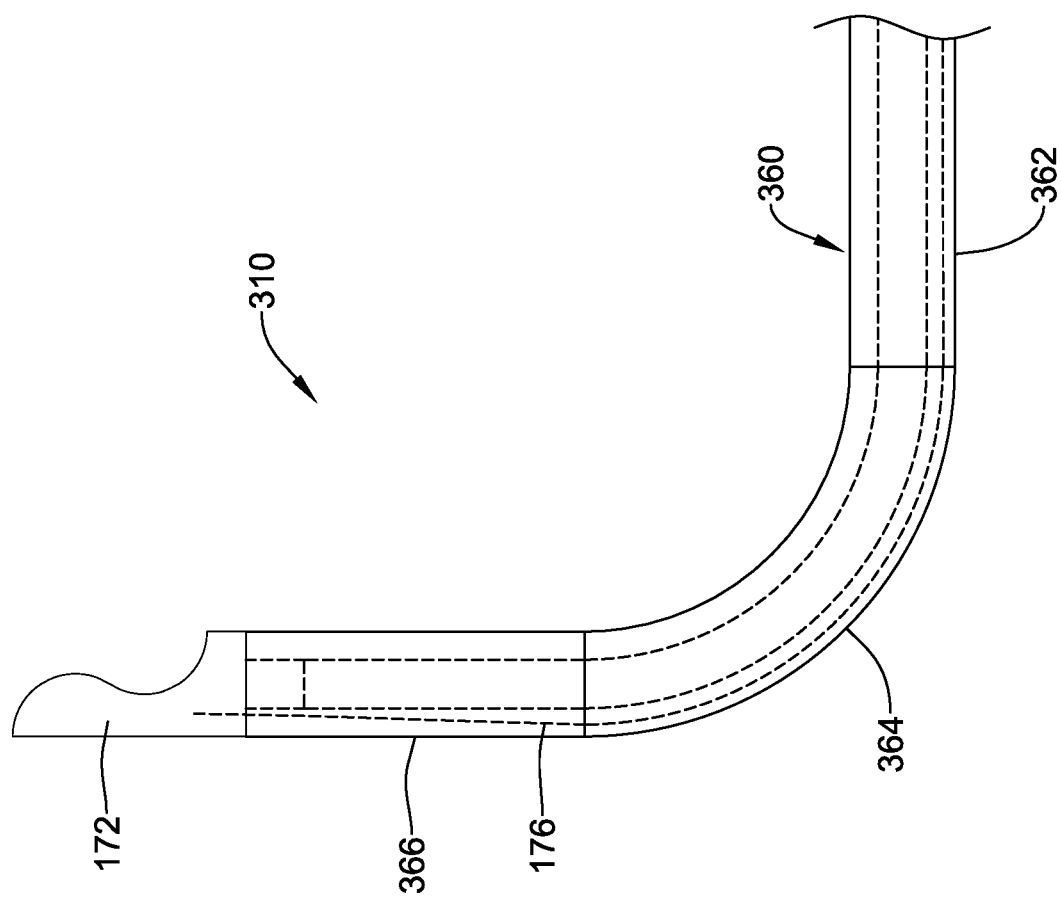

FIGS. 18 and 19 illustrate an alternative configuration of an elongate shaft 310 for delivering the medical device 180 (not shown). The elongate shaft 310 may be formed and/or manufactured using any of the methods described herein. The elongate shaft 310 may include a polymeric sheath 350 having a lumen extending therethrough. The elongate shaft 310 may include a metallic tubular member 320 disposed over a proximal portion of the polymeric sheath 350, in a manner consistent with the configuration(s) described herein with respect to the elongate shaft 110. In at least some embodiments, the metallic tubular member 320 may be constructed and/or may have physical characteristics similar to or the same as the metallic tubular member 120 described herein, and said description is not repeated. The elongate shaft 310 may include a polymeric tubular member 360 disposed over a distal portion of the polymeric sheath 350 and a distal portion of the metallic tubular member 320, in a manner consistent with the configuration(s) described herein with respect to the elongate shaft 110. The elongate shaft 310 may include the longitudinal support filament 176 extending along the distal portion of the polymeric sheath 350 and the distal portion of the metallic tubular member 320, in a manner consistent with the configuration(s) described herein with respect to the elongate shaft 110. The elongate shaft 310 may include the proximal coupler 172 fixedly attached to the distal end of the longitudinal support filament 176, in a manner consistent with the configuration(s) described herein with respect to the elongate shaft 110.

In some examples, the polymeric tubular member 360 may secure the longitudinal support filament 176 relative to the polymeric sheath 350 and the metallic tubular member 320, in a manner consistent with the configuration(s) described herein with respect to the elongate shaft 110. The polymeric tubular member 360 may include a proximal portion 362, a distal portion 366, and a middle portion 364 disposed longitudinally between the proximal portion 362 and the distal portion 366. In at least some embodiments, the middle portion 364 may extend continuously from the proximal portion 362 to the distal portion 366. The middle portion 364 may have a lower bending stiffness than the proximal portion 362 and the distal portion 366. For example, the proximal portion 362 may be formed from a first material, the middle portion 364 may be formed from a second material, and the distal portion 366 may be formed from a third material. In some embodiments, the second material may be different from the first material and/or the third material. In some embodiments, the third material may be the first material. Other configurations are also contemplated. Accordingly, the middle portion 364 may define a preferential bending location of the elongate shaft 310, as seen in FIG. 19.

The longitudinal support filament 176 may extend within the proximal portion 362, the middle portion 364, and the distal portion 366 of the polymeric tubular member 360. As such, the longitudinal support filament 176 may substantially limit and/or prevent axial stretching of the polymeric tubular member 360 and/or the elongate shaft 310. While the second material of the polymeric tubular member 360 may be more susceptible to axial stretch due to its lower bending stiffness than the first material and the third material, the longitudinal support filament 176 may have a high modulus of elasticity as discussed herein, thereby limiting and/or preventing axial stretch of the elongate shaft 310 within the middle portion 364 of the polymeric tubular member 360. In some embodiments, the radial and/or circumferential location of the longitudinal support filament 176 may further define preferential bending characteristics of the elongate shaft 310, such as direction of bending relative to the central longitudinal axis of the elongate shaft 310.

Figure 20:
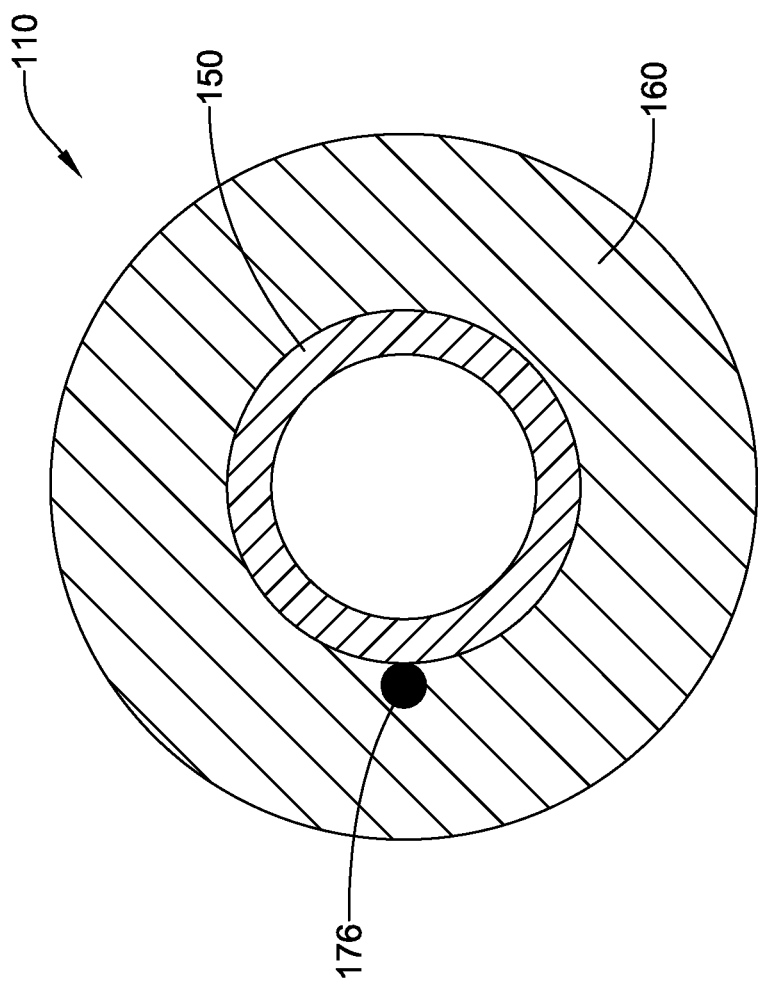
FIG. 20 is a cross-section of the delivery shaft.

FIG. 20 is a cross-sectional view illustrating one example configuration of the longitudinal support filament 176 within the elongate shaft 110. The cross-section shown in FIG. 20 may be taken at a location distal of the metallic tubular member 120 and proximal of the proximal coupler 172. As described herein, the longitudinal support filament 176 may be in direct contact with the polymeric sheath 150 and/or the polymeric tubular member 160. In some embodiments, the longitudinal support filament 176 may be embedded within and/or surrounded by the polymeric tubular member 160 alongside the polymeric sheath 150. Other configurations consistent with the instant disclosure are also contemplated. The skilled person will recognize that the configuration may be applied in any of the configurations of an elongate shaft (e.g., ref. 210, 310) disclosed herein.

Figure 21:
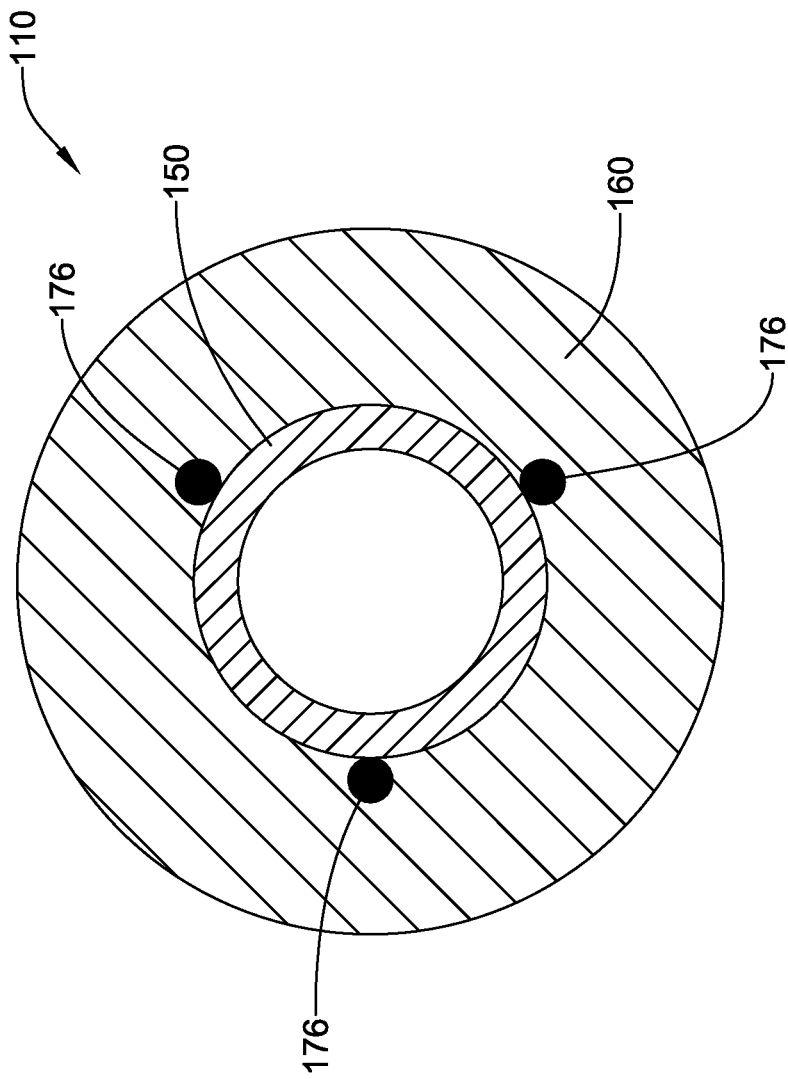
FIG. 21 is a cross-section of an alternative configuration of the delivery shaft.

FIG. 21 is a cross-sectional view illustrating an alternative configuration of the elongate shaft 110. In the alternative configuration of FIG. 21, the elongate shaft 110 may include a plurality of longitudinal support filaments 176. In the illustrated example, the plurality of longitudinal support filaments 176 includes three longitudinal support filaments circumferentially spaced apart around the polymeric sheath 150. Though not expressly illustrated, other configurations including two longitudinal support filaments, four longitudinal support filaments, five longitudinal support filaments, six longitudinal support filaments, or another suitable number of longitudinal support filaments are also contemplated. In some embodiments, the plurality of longitudinal support filaments 176 may be circumferentially spaced apart equally around the polymeric sheath 150. Such a configuration may prevent formation or introduction of preferential bending characteristics. In some embodiments, the plurality of longitudinal support filaments 176 may be arranged unequally and/or irregularly around the polymeric sheath 150, so as to define and/or induce preferential bending characteristics.

The cross-section shown in FIG. 21 may be taken at a location distal of the metallic tubular member 120 and proximal of the proximal coupler 172. Similar to some configurations disclosed herein, the plurality of longitudinal support filaments 176 may be in direct contact with the polymeric sheath 150 and/or the polymeric tubular member 160. In some embodiments, the plurality of longitudinal support filaments 176 may be embedded within and/or surrounded by the polymeric tubular member 160 alongside the polymeric sheath 150. Other configurations consistent with the instant disclosure are also contemplated. The skilled person will recognize that the configuration may be applied in any of the configurations of an elongate shaft (e.g., ref. 210, 310) disclosed herein.

The materials that can be used for the various components of the delivery shaft (and/or other elements disclosed herein) and the various components thereof disclosed herein may include those commonly associated with medical devices. For simplicity purposes, the following discussion makes reference to the delivery shaft. However, this is not intended to limit the devices and methods described herein, as the discussion may be applied to other elements, members, components, or devices disclosed herein, such as, but not limited to, the elongate shaft, the release wire, the polymeric sheath, the metallic tubular member, the polymeric tubular member, the release mechanism, the longitudinal support filament, the microcatheter, etc. and/or elements or components thereof.

In some embodiments, the delivery shaft and/or other elements disclosed herein may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "super-elastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some examples, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (also distinguishable by its composition), which may accept only about 0.2 to 0.44 percent strain before plastically deforming.

In some examples, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In some examples, portions or all of the delivery shaft and/or other elements disclosed herein may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the delivery shaft and/or other elements disclosed herein. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the delivery shaft and/or other elements disclosed herein to achieve the same result.

In some embodiments, a degree of Magnetic Resonance Imaging (MRI) compatibility is imparted into the delivery shaft and/or other elements disclosed herein. For example, the delivery shaft and/or components or portions thereof may be made of a material that does not substantially distort the image and create substantial artifacts (e.g., gaps in the image). Certain ferromagnetic materials, for example, may not be suitable because they may create artifacts in an MRI image. The delivery shaft or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some examples, the delivery shaft and/or other elements disclosed herein may be made from or include a polymer or other suitable material. Some suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyimide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the delivery shaft and/or other elements disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some examples, the delivery shaft and/or other elements disclosed herein may include and/or be formed from a textile material. Some examples of suitable textile materials may include synthetic yarns that may be flat, shaped, twisted, textured, pre-shrunk or un-shrunk. Synthetic biocompatible yarns suitable for use in the present disclosure include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Synthetic yarns may be or may include a metallic yarn or a glass or ceramic yarn or fiber, such as yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun types. The type and denier of the yarn chosen may be selected in a manner which forms a biocompatible and implantable prosthesis and, more particularly, a vascular structure having desirable properties.

In some embodiments, the delivery shaft and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethyl ketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and me s alamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps, without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A method of manufacturing an elongate shaft for delivery of a medical device, comprising:
   extruding a polymeric tubular member and a longitudinal support filament over a first polymeric sheath, while the first polymeric sheath is disposed on a mandrel, to form a composite tubular member;
   removing the mandrel from within the composite tubular member;
   sliding a metallic tubular member over a second polymeric sheath and securing a distal end of the second polymeric sheath to a distal end of the metallic tubular member;
   placing the composite tubular member, with the mandrel removed, over a distal portion of the metallic tubular member; and
   reflowing a proximal portion of the polymeric tubular member onto the distal portion of the metallic tubular member to secure the longitudinal support filament relative to the metallic tubular member.

2. The method of claim 1, further comprising removing a proximal portion of the first polymeric sheath from within the composite tubular member before placing the composite tubular member over the distal portion of the metallic tubular member.

3. The method of claim 2, wherein reflowing the proximal portion of the polymeric tubular member secures the longitudinal support filament against an outer surface of the distal portion of the metallic tubular member.

4. The method of claim 1, further comprising fixedly attaching a proximal coupler to a distal end of the longitudinal support filament.

5. The method of claim 4, wherein a distal portion of the polymeric tubular member is removed to expose the distal end of the longitudinal support filament prior to fixedly attaching the proximal coupler.

6. The method of claim 1, wherein the metallic tubular member includes a proximal portion and a distally tapered portion extending from the proximal portion to the distal portion.

7. The method of claim 6, wherein after reflowing a proximal portion of the polymeric tubular member, a proximalmost end of the polymeric tubular member is disposed distal of the distally tapered portion of the metallic tubular member.

8. The method of claim 1, wherein the polymeric tubular member is extruded such that it includes a proximal portion formed from a first polymeric material and a distal portion formed from a second polymeric material different from the first polymeric material.

* * * * *